United States Patent
Patwari et al.

(10) Patent No.: US 12,254,533 B2
(45) Date of Patent: Mar. 18, 2025

(54) PROCESS FOR ITERATIVELY RECONSTRUCTING IMAGES USING DEEP LEARNING

(71) Applicant: Siemens Healthcare GmbH, Erlangen (DE)

(72) Inventors: Mayank Patwari, Erlangen (DE); Ralf Gutjahr, Nuremberg (DE); Rainer Raupach, Heroldsbach (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 538 days.

(21) Appl. No.: 17/669,578

(22) Filed: Feb. 11, 2022

(65) Prior Publication Data
US 2022/0277497 A1 Sep. 1, 2022

(30) Foreign Application Priority Data
Feb. 26, 2021 (EP) .................................. 21159672

(51) Int. Cl.
| | |
|---|---|
| *G06N 3/08* | (2023.01) |
| *G06N 3/045* | (2023.01) |
| *G06T 11/00* | (2006.01) |
| *A61B 6/03* | (2006.01) |

(52) U.S. Cl.
CPC ............ *G06T 11/003* (2013.01); *G06N 3/045* (2023.01); *G06N 3/08* (2013.01); *A61B 6/032* (2013.01); *G06T 2207/10081* (2013.01); *G06T 2207/20081* (2013.01); *G06T 2207/20084* (2013.01); *G06T 2211/421* (2013.01); *G06T 2211/424* (2013.01)

(58) Field of Classification Search
CPC ......... G06T 11/003; G06T 2207/10081; G06T 2207/20081; G06T 2207/20084; G06T 2211/421; G06T 2211/424; G06T 11/006; G06N 3/045; G06N 3/08; A61B 6/032
USPC ......................................................... 382/131
See application file for complete search history.

(56) References Cited

U.S. PATENT DOCUMENTS

| | | | | |
|---|---|---|---|---|
| 8,121,361 | B2* | 2/2012 | Ernst .................... | A61B 5/7292 |
| | | | | 382/128 |
| 11,699,514 | B2* | 7/2023 | Kozloski ................ | G16H 30/40 |
| | | | | 706/12 |
| 2022/0165395 | A1* | 5/2022 | Patil .................... | G06F 11/3058 |

OTHER PUBLICATIONS

Wang, Wei et al: "An End-to-End Deep Network for Reconstructing CT Images Directly From Sparse Sinograms"; IEEE Transactions on Computational Imaging, IEEE; vol. 6; Nov. 19, 2020 (Nov. 19, 2020); pp. 1548-1560; XP011824375.

(Continued)

*Primary Examiner* — Charlotte M Baker
(74) *Attorney, Agent, or Firm* — Harness, Dickey & Pierce, P.L.C.

(57) ABSTRACT

In a computer-implemented method of iteratively reconstructing images or a volume using deep learning and a computer-implemented method of training, projection filter parameter(s) of a projection (joint) bilateral filter, (J)BF, are automatically tuned by a first trained neural network based on data of projections of an imaging procedure. Volume filter parameter(s) of a volume (J)BF are automatically tuned by a second trained neural network based on data of a volume backward-projected from projections filtered by the projection (joint) bilateral filter using the automatically tuned projection filter parameter(s). A volume filtered by the volume (J)BF is output as the reconstructed images or volume, in case the filtered volume meets a predefined quality criterion.

22 Claims, 6 Drawing Sheets

(56) References Cited

OTHER PUBLICATIONS

Bellman, "Dynamic Programming," Science, vol. 153, No. 3731, pp. 34-37, 1966.
"Bilateral Filtering for Gray and Color Images", available at http://homepages.inf.ed.ac.uk/rbf/CVonline/LOCAL_COPIES/MANDUCHI1/Bilateral_Filtering.html.
Manduca et al.: "Projection space denoising with bilateral filtering and CT noise modeling for dose reduction in CT", Medical Physics, vol. 36, No. 11, pp. 4911-4919, 2009.
Patwari, Mayank et al: "JBFnet—Low Dose CT Denoising by Trainable Joint Bilateral Filtering"; Sep. 29, 2020 (Sep. 29, 2020); Advances in Intelligent Data Analysis XIX; [Lecture Notes in Computer Science; Lect.Notes Computer], Springer International Publishing, Cham; pp. 506-515; XP047563859.
Yin Xiangrui et al: "Domain Progressive 3D Residual Convolution Network to Improve Low-Dose CT Imaging"; IEEE Transactions on Medical Imaging, IEEE Service Center, Piscataway, NJ, US; vol. 38; No. 12; Dec. 2019 (Dec. 2019); pp. 2903-2913; XP011758305.
Kingma—Adam: A Method for Stochastic Optimization—Published as a conference paper at ICLR 2015; 2015.
C. H. Mccollough, "Low Dose CT Grand Challenge", 2016.
Wooram, Kang et al: "Low Dose Helical CBCT denoising by using domain filtering with deep reinforcement learning"; arxiv.org, Cornell University Library, 201 Olin Library Cornell University Ithaca, NY 14853; Apr. 2, 2021 (Apr. 2, 2021); XP081931541.

\* cited by examiner

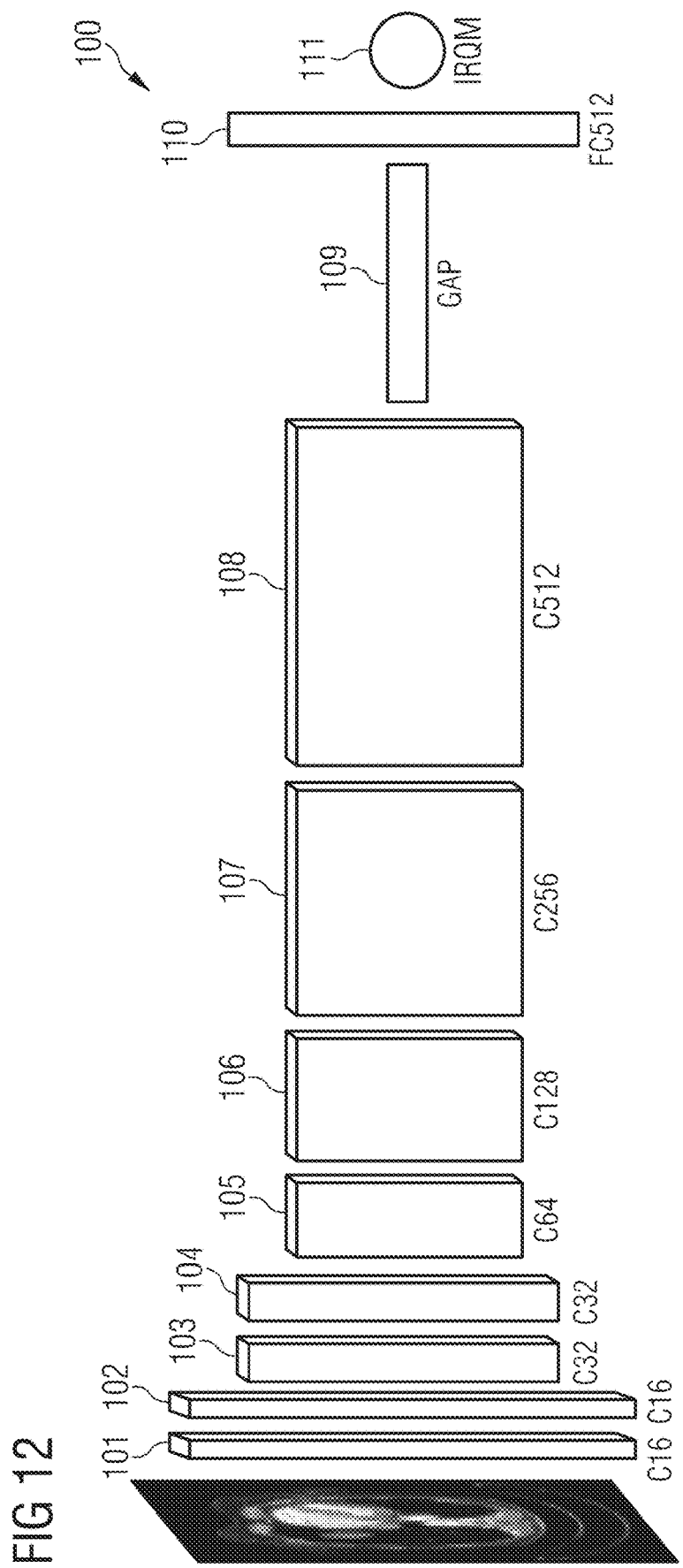

PROCESS FOR ITERATIVELY RECONSTRUCTING IMAGES USING DEEP LEARNING

CROSS-REFERENCE TO RELATED APPLICATION(S)

The present application claims priority under 35 U.S.C. § 119 to European Patent Application No. 21159672.1, filed Feb. 26, 2021, the entire contents of which are incorporated herein by reference.

FIELD

Example embodiments are related to computer-implemented methods of iteratively reconstructing images or a volume, for example medical images or a medical volume like computer tomography (CT) images or a CT volume, using deep learning and computer-implemented methods of training a first neural network for automatically tuning a projection filter parameter for a projection (joint) bilateral filter ((J)BF) for projections and a second neural network for automatically tuning a volume filter parameter for a volume (J)BF for volumes as well as corresponding computer program products, computer-readable media, and/or data processing systems.

BACKGROUND

Medical imaging techniques such as computed tomography, CT, magnetic resonance tomography, MRT, X-ray imaging, ultrasound imaging and so on are increasingly common for medical diagnoses and treatments. In part this is due to an increased interest and improved results using artificial neural networks for analyzing medical images, i.e. medical imaging results, for providing automated analyses or support to a trained physician.

However, such techniques rely heavily on the availability of comparatively noise-free medical images. One reason for this is that even small deviations from trained patterns or structures may cause an artificial neural network to detect an abnormality which could mean that a position within the medical image is flagged as cancerous, for example. In order to reduce or minimize the rate of such false positives caused by noise in the medical images methods for de-noising images are applied.

Usually, image processing operations such as denoising processes are linear. This makes standard image processing operations less suitable for medical images which have non-stationary characteristics. An example of this is non-stationary noise in radiological imaging. Global use of linear image processing would reduce image quality in this case. Non-linear operations also exist; however, they are less effective and some cases computationally expensive. Moreover, most non-linear approaches require input parameters, which are estimated using complex and occasionally non-deterministic methods.

In the conventional art, parameter values for non-linear techniques are often fixed and/or tuned manually until the quality is considered acceptable. However, these methods are not adaptive and in some cases or regions of a medical image the parameter settings may even impair image quality. It is in general impractical to tune a parameter value manually for every region in the image, resulting in suboptimal image quality.

For example, bilateral filtering has been discussed in scientific publications such as "Bilateral Filtering for Gray and Color Images", available at http://homepages.inf.ed.ac.uk/rbf/CVonline/LOCAL_COPIES/MANDUCHI1/Bilateral_Filtering.html. The basic idea underlying bilateral filtering concerns doing in the value range of the pixels (i.e. spatial positions) of an image what traditional filters do in its domain. Two pixels can be close to one another (domain), that is, occupy a nearby spatial location, or they can be similar to one another (range), that is, have similar values, such as similar colour values or the like. Bilateral filtering in the context of medical imaging data is known, for example, from the scientific publication by Manduca, A. et al.: "Projection space denoising with bilateral filtering and CT noise modelling for dose reduction in CT", Medical Physics, vol. 36, no. 11, pp. 4911-4919, 2009.

Moreover, deep learning methods are being experimented with in the context of image processing operations. However, most experimental deep learning methods rely on the use of extremely deep neural networks with over one hundred million trainable parameters. These networks therefore function as black boxes and their performance can rarely be explained or accounted for. Especially in the field of medical applications, explainability and accountability are highly valued. Therefore, using said techniques in any regulated setting may be relatively difficult.

In particular, a disadvantage in CT imaging is the use of damaging x-ray radiation for scanning. To reduce patient harm, the radiation dose of CT is to be kept as low as possible. However, this results in noise in the collected projections and subsequently in the reconstructed volumes. Such noise reduces the clinical value of CT scans.

Noise removal in CT is usually performed in conjunction with the reconstruction process. Iterative CT reconstruction based on (weighted) filtered back projection ((W)FBP) is currently offered on most clinical scanners. This type of reconstruction uses noise removal filters in the projection, i.e. the projection, domain as well as the reconstructed volume domain to remove noise, while using the iterative nature of the process to resolve geometric artefacts. Examples of iterative reconstruction algorithms include Siemens ADMIRE and Canon AIDR. Iterative reconstruction involves solving the inverse problem of getting an image, projecting the image forward using a simulated scanner, and comparing the simulated projections to the data obtained with the scanner. The inverse problem solver is then updated and the process is then repeated. A downside of this iterative technique is that it is computationally intensive, requiring multiple forward and backward projections.

Model based iterative reconstruction is a more accurate iterative reconstruction variant which includes knowledge of the scanning system into the process.

Statistical reconstruction is another popular algorithm for CT reconstruction. Variants of these include the SIRT and SART algorithms for CT reconstruction. A downside of these techniques is the time consuming nature and incomplete artefact removal.

Also, deep learning approaches have been successfully applied to the CT denoising problem. Most deep learning approaches for CT denoising are formulated in the form of image translation tasks, where CNNs learn a mapping from a noisy CT volume to a clean CT volume. Some networks also attempt to denoise CT volumes iteratively for better control of the denoising processes. Also a few methods attempt to model the reconstruction process or parameters or apply separate deep neural networks, trained separately, for denoising in the projection and volume domains. Deep reinforcement learning has been applied to tune pixel-wise parameters for solving the reconstruction and denoising problems. As there are usually several hundreds of thousand parameters involved, interpretability may be impractical.

SUMMARY

At least one example embodiment provides a method (or improved method) of iteratively reconstructing images using deep learning as well as a corresponding improved computer program, a corresponding improved non-transitory computer-readable medium and/or a corresponding improved data processing system.

According to a first aspect of example embodiments, a computer-implemented method of iteratively reconstructing images or a volume, in particular medical images or a medical volume like computer tomography (CT) images or a CT volume, using deep learning, comprises the following steps:

d) Automatically tuning a spatial projection filter parameter $\sigma s,sin$ and additionally or alternatively an intensity projection filter parameter $\sigma i,sin$ of a projection (joint) bilateral filter ((J)BF), i.e. a projection bilateral filter (BF) or a projection joint bilateral filter (JBF), F sin by a first trained neural network NNsin based on data of projections, in particular sinograms, of an imaging procedure, in particular a medical (CT) scan, in case the first iteration starts at step d), or on data of forward projected projections, otherwise;

e) Filtering the projections with the projection (J)BF F sin using the respective automatically tuned projection filter parameters $\sigma s,sin/\sigma i,sin$;

f) Backward-projecting a volume from the projections of the imaging procedure, in particular the medical (CT) scan, in case the first iteration starts at step f), or from the filtered projections, otherwise, using a (weighted) filtered back-projection ((W)FBP), in particular the algorithm of Feldkamp, Davis and Kress (FDK), the FBP algorithm or the WFBP algorithm;

g) Automatically tuning a spatial volume filter parameter $\sigma s,vol$ and additionally or alternatively an intensity volume filter parameter $\sigma i,vol$ of a volume (J)BF, i.e. a volume BF or a volume JBF, Fvol by a second trained neural network NNvol based on data of a volume of the imaging procedure, in particular a medical (CT) scan, in case the first iteration starts at step g), or on the backward-projected volume, otherwise;

h) Filtering the volume with the volume (J)BF Fvol using the respective automatically tuned volume filter parameters $\sigma s,vol/\sigma i,vol$;

i) Forward-projecting projections from the volume of the imaging procedure, in particular a medical (CT) scan, in case the first iteration starts at step i), or from the filtered volume and returning to step d), in case the filtered volume does not meet a predefined quality criterion, otherwise; and j) Outputting the filtered volume as the reconstructed medical images or volume, in particular as the reconstructed CT images or volume, in case the filtered volume meets the predefined quality criterion.

The first iteration starts at one of the group comprising step d); step f); step g) and step i).

According to a second aspect of example embodiments, a computer program product comprises instructions which, when executed on a data processing system, cause the system to execute the steps of the method according to the first aspect of example embodiments.

According to a third aspect of example embodiments, a computer-readable medium comprises the computer program product according to the second aspect of example embodiments.

According to a fourth aspect of example embodiments, a data processing system for iteratively reconstructing medical images or a medical volume using deep learning, that is in particular configured to execute the steps of the method according to the first aspect of example embodiments, comprises an input module configured to receive projections and/or volumes of a imaging procedure, in particular a medical (CT) scan; an output module configured to be communicatively connected with and to provide volumes to external modules; a projection (joint) bilateral filter ((J)BF), i.e. a projection bilateral filter (BF) or a projection joint bilateral filter JBF, F sin; a volume (J)BF, i.e. a volume BF or a volume JBF, Fvol; a backward-projector; a forward-projector; a first trained neural network NNsin; and a second trained neural network NNvol. The projection (J)BF F sin is configured to filter projections. The volume (J)BF Fvol is configured to filter volumes. The backward-projector is communicatively connected to the (J)BF F sin and configured to backward-project volumes from projections. The forward-projector is communicatively connected to the volume (J)BF Fvol and configured to forward-project projections from volumes. The first trained neural network NNsin is communicatively connected to the forward-projector and configured to receive data of projections as input and to provide a spatial projection filter parameter $\sigma s,sin$ and additionally or alternatively an intensity projection filter parameter $\sigma i,sin$ of the projection (J)BF F sin as output. The second trained neural network NNvol is communicatively connected to the backward-projector and configured to receive data of a volume as input and to provide a spatial volume filter parameter $\sigma s,vol$ and additionally or alternatively an intensity volume filter parameter $\sigma i,vol$ of the volume (J)BF Fvol as output. The input module is communicatively connected to at least one of the group comprising first trained neural network NNsin; the second trained neural network NNvol; the backward-projector; and/or the forward-projector. The first trained neural network NNsin is configured to automatically tune the spatial projection filter parameter $\sigma s,sin$ and additionally or alternatively the intensity projection filter parameter $\sigma i,sin$ of a of the (J)BF F sin based on data of the projections of the imaging procedure, in particular a medical (CT) scan, or on data of the forward projected projections. The projection (J)BF F sin is configured to filter the projections using the respective automatically tuned projection filter parameter(s) $\sigma s,sin/\sigma i,sin$. The backward-projector is configured to backward-project a volume from the projections of the imaging procedure, in particular a medical (CT) scan, or from the filtered projections using a (weighted) filtered back-projection ((W)FBP). The second trained neural network NNvol is configured to automatically tune the spatial volume filter parameter $\sigma s,vol$ and additionally or alternatively the intensity volume filter parameter $\sigma i,vol$ of the volume (J)BF Fvol based on the received data of the volume of the imaging procedure, in particular a medical (CT) scan, or on the backward-projected volume. The volume (J)BF is configured to filter the volume using the respective automatically tuned volume filter parameter(s) $\sigma s,vol/\sigma i,vol$. The forward-projector is configured to forward-project projections from the volume of the imaging procedure, in particular a medical (CT) scan, or from the filtered volume. The output module is communicatively connected to the volume (J)BF Fvol and configured to provide the filtered volume to external modules, in case the filtered volume meets a predefined quality criterion.

According to a fifth aspect of example embodiments a CT system comprises a CT scanner; the data processing system according to the fourth aspect of example embodiments; and an output device. The data processing system is communicatively connected to a controller of the CT scanner or integrated in the controller of the CT scanner. The output device is communicatively connected to the data processing system. The data processing system is configured to receive data of projections and additionally or alternatively of volumes of CT scans conducted by the CT scanner via the input module of the data processing system as input. The data processing system is further configured to provide filtered volumes to the output device via the output module of the data processing system.

According to a sixth aspect of example embodiments, a computer-implemented method of training a first neural network NNsin for automatically tuning a projection filter parameter σs,sin/σi,sin for a projection (joint) bilateral filter ((J)BF) F sin for projections and a second neural network NNvol for automatically tuning a volume filter parameter σs,vol/σi,vol for a volume (J)BF Fvol for volumes comprises the following steps:

t1) Providing a training set comprising training data of training volumes, in particular CT training volumes;

t2) Providing a first neural network NNsin configured to receive data of projections as input and to provide a spatial projection filter parameter σs,sin and additionally or alternatively an intensity projection filter parameter σi,sin of a projection (J)BF F sin as output;

t3) Providing a second neural network NNvol configured to receive data of a volume as input and to provide a spatial volume filter parameter σs,vol and additionally or alternatively an intensity volume filter parameter σi,vol of a volume (J)BF Fvol as output; and t4) Training the first neural network NNsin and the second neural network NNvol based on a respective reward for each of the first and second neural network;

According to a seventh aspect of example embodiments, a computer program product comprises instructions which, when executed on a data processing system, cause the system to execute the steps of a method according to the sixth aspect of example embodiments.

According to an eighth aspect of example embodiments a computer-readable medium comprises the computer program product according to the seventh aspect of example embodiments.

According to a ninth aspect of example embodiments, a data processing system comprises one or more processors or other processing circuitry configured to execute the steps of a method according to the sixth aspect of example embodiments.

According to one or more example embodiments, medical images or a medical volume, in particular CT images or a CT volume, is iteratively reconstructed using (weighted) filtered back-projection ((W)FBP). The quality of the reconstructed images or volume is improved by using deep learning in both the projection (raw data or projection) domain and volume (image) domain. This deep iterative reconstruction may utilize reinforcement learning to train the respective neural networks to tune filter parameters within both the projection domain and the volume domain.

The iterative reconstruction of medical images or a medical volume, according to one or more example embodiments, involves a reconstruction technique which functions in a single pass, eg. (W)FBP, and a simple forward projector to generate projections (projections).

The steps d) to i) are executed iteratively until the filtered volume meets the predefined quality criterion. The first iteration of steps d) to i) can start at step d), step f), step g) or step i).

A method according to the first aspect of example embodiments, may further comprise the following (non-iterative) steps before the iterative steps d) to i):

a) Providing the first trained neural network NNsin configured to receive data of projections as input and to provide a spatial projection filter parameter σs,sin and additionally or alternatively an intensity projection filter parameter σi,sin of the projection (J)BF F sin as output;

b) Providing the second trained neural network NNsin configured to receive data of a volume as input and to provide a spatial volume filter parameter σs,vol and additionally or alternatively an intensity volume filter parameter σi,vol of the volume (J)BF Fvol as output; and c) Receiving data of the projections and additionally or alternatively data of the volume of the imaging procedure, in particular a medical (CT) scan.

Firstly, the first trained neural network NNsin for tuning the projection filter parameters and the second trained neural network NNvol for tuning the volume filter parameters may be provided (steps a) and b)). The first and second neural network may be implemented on a common or each on a separate machine learning module. The machine learning module(s) may be a software module or a hardware module (e.g. data processing system, dedicated processing unit, etc.).

The first neural network NNsin is trained to automatically tune the spatial projection filter parameter σs,sin and additionally or alternatively the intensity projection filter parameter σi,sin of the projection (J)BF F sin for filtering the projections (of the imaging procedure, in particular a medical (CT) scan, or forward-projected from a volume e.g. of the same or a previous iteration).

The second neural network NNvol is trained to automatically tune the spatial volume filter parameter σs,vol and additionally or alternatively the intensity volume filter parameter σi,vol of the volume (J)BF Fvol for filtering the volume (of the imaging procedure, in particular a medical (CT) scan, or backward-projected from projections e.g. of the same or a previous iteration).

The projection and volume (J)BF are both (J)BFs. A BF is a non-linear filter combining a spatial smoothing filter c and an intensity filter s. The spatial filter c is based on a closeness function which accounts for spatial distance between a central pixel/voxel x and its neighbours o:

$$c(x, o) = G_{\sigma_s}(x - o) = \frac{1}{\sqrt{2\pi}\,\sigma_s} e^{-\left(\frac{(d(x,o))^2}{2\sigma_s^2}\right)},$$

$$d(x, o) = \|x - 0\| = \sqrt{(x_1 - o_1)^2 + (x_2 - o_2)^2 + (x_3 - o_3)^2},$$

where σs is the amount of spatial smoothing and d(x,o) is the distance between pixel/voxel x and its neighbour o. The intensity filter s based on a similarity function between intensities I of the central pixel/voxel x and its neighbours o:

$$s(x, o) = G_{\sigma_i}(I(x) - I(o)) = \frac{1}{\sqrt{2\pi}\,\sigma_i} e^{-\left(\frac{(\delta(I(x),I(o)))^2}{2\sigma_i^2}\right)},$$

$$\delta(I(x), I(o)) = \|I(x) - I(o)\|,$$

where σi is the amount of intensity smoothing and δ is the difference between the intensities I of the central pixel/voxel x and its neighbour o. In both filters, the constant $\sqrt{2\pi}$ may be omitted as it would be compensated during training of the first and second neural network. The volume or rather the projection FT filtered with the BF is calculated via the following equation:

$$FT(x) = \frac{\sum_{o \in N(x)} IN(o) G_{\sigma_s}(x-o) G_{\sigma_i}(I(x) - I(o))}{\sum_{o \in N(x)} G_{\sigma_s}(x-o) G_{\sigma_i}(I(x) - I(o))},$$

where IN is the input (i.e. noisy) volume or rather projection and N(x) is the considered neighbourhood of the central pixel/voxel x. The BF reduces noise and preserves edges. A JBF has the same structure as a BF and additionally uses a deep learned guidance image to further denoise the image/volume or projection. The volume or rather the projection FT filtered with the JBF is calculated via the following equation:

$$FT(x) = \frac{\sum_{o \in N(x)} IN(o) G_{\sigma_s}(x-o) G_{\sigma_i}(I_g(x) - I_g(o))}{\sum_{o \in N(x)} G_{\sigma_s}(x-o) G_{\sigma_i}(I_g(x) - I_g(o))},$$

where Ig is the intensity in the guidance image (projection or volume).

The filter for the projection F sin, according to one or more example embodiments, is a BF or a JBF. The filter for the volume Fvol, according to one or more example embodiments, is a BF or a JBF.

The first and second neural network for automatically tuning the projection and volume filter parameters of the respective (J)BFs may comprise an input layer configured to receive data of projections or rather of a volume. The first and second neural network may further comprise an output layer configured to output a value of one or of each filter parameter or rather a change action for one or for each filter parameter. Between the input and output layer the first and second neural network may comprise at least one layer comprising at least two neurons.

Artificial neural networks (ANN) or short neural networks (NN) are systems, in particular computing systems, inspired by biological neural networks that constitute animal brains. NNs "learn" to perform tasks by considering (labelled) examples called training data, generally without being designed with any task-specific rules. During an initial learning or training phase NNs automatically generate identifying characteristics from the (labelled) training data. NNs comprise a collection of connected nodes called artificial neurons, which loosely model the neurons in a biological brain. Each connection (synapses in the biological brain) can transmit a signal from one node to another. A node that receives a signal can process it and then signal to subsequent neurons connected to it. In common NN implementations, the signal at a connection between nodes is a real number (e.g. 0 . . . 1), and the output of each artificial neuron is computed by some non-linear function of the sum of its inputs (from other nodes). The connections between nodes are called "edges". The edges in NNs may each have a weight that is adjusted during training of the NNs. The weight increases or decreases the strength of the signal at the corresponding edge. Nodes may each have a threshold such that the signal is only sent if an aggregate signal exceeds that threshold. Typically, nodes are aggregated into layers. Different layers may perform different kinds of transformations on their inputs. Signals travel from a first layer or input layer to a last layer or output layer, possibly after traversing the layers multiple times.

In other words, an NN is a network of simple elements, the so-called nodes or artificial neurons, which receive input. After receiving input the nodes change their internal state (activation) according to that input, and produce output depending on the input and activation. The network forms by connecting the output of certain nodes to the input of other nodes forming a directed, weighted graph. The weights as well as the functions that compute the activation of each node can be modified during initial learning/training, which is governed by a learning rule or paradigm.

A node/neuron receiving an input from at least one predecessor node/neuron consists of the following components: an activation, the node's state, depending on a discrete time parameter, optionally a threshold, which stays fixed unless changed by a learning/training function, an activation function (e.g. hyperbolic tangent function, sigmoid function, softmax function, rectifier function etc.) that computes the new activation at a given time and the net input and an output function computing the output from the activation (often the output function is the identity function). An important characteristic of the activation function is that it provides a smooth transition as input values change, i.e. a small change in input produces a small change in output.

An input node has no predecessor but serves as input interface for the whole NN. Similarly an output node has no successor and thus serves as output interface of the whole NN. An NN consists of edges/connections, each edge transferring the output of a node (predecessor) to the input of another, succeeding node (successor). Additionally to the assigned weight an edge may have a bias term added to a total weighted sum of inputs to serve as a threshold to shift the activation function. The propagation function computes the input to the succeeding node (successor) from the outputs of preceding nodes (predecessors) and may include the bias value.

Secondly, in case the iteration starts at step d), data of projections of the imaging procedure, in particular a medical (CT) scan preferably using the CT scanner, are received as input to the first trained neural network NNsin.

In case the iteration starts at step f), data of projections of the imaging procedure, in particular a medical (CT) scan preferably using the CT scanner, are received as input to the (weighted) filtered backward projection or rather the backward-projector.

In case the iteration starts at step g), data of a volume of the imaging procedure, in particular a medical (CT) scan preferably using the CT scanner, are received as input to the second trained neural network NNvol.

In case the iteration starts at step i), data of a volume of the imaging procedure, in particular a medical (CT) scan preferably using the CT scanner, are received as input to the forward-projection or rather the forward-projector.

Projections are any raw-data acquired during an imaging process, in particular a medical scan like CT, magnetic resonance imaging (MRI), ultra sound imaging, and the like. Preferably, the projections are sinograms acquired during a CT scan of a subject. Thereby, the subject is radiated with x-ray beams from one side and the remaining radiation is collected at the opposite side. The x-ray beam may be emitted as point (0D), line (1D), or preferably cone (2D) and the resulting projection may accordingly be one intensity (0D), an array of intensities (1D), or a matrix/an image of intensities (2D). The data of projections may be one or more intensity values of one or more of the projections. For example, the data of projections may be the intensity value of one central pixel x and the intensity values of a predefined amount of neighbours o of the central pixel x of one of the projections.

The tuning of filter parameters and filtering of the projections and volume are iteratively executed. As an example, one iteration staring a step d) is described in the following. However, as already mentioned, the first iteration and thus any subsequent iteration may start at either step f) or step g) or step i) instead of step d).

In the first iteration, the received data of projections of the imaging procedure is used as input to the first neural network NNsin. Alternatively, forward-projected projections form a volume of the imaging procedure (medical (CT) scan) may be used as input to the first trained neural network NNsin in the first iteration. In the subsequent iterations, forward-projected projections based on volumes of the respective previous iteration are used as input to the first trained neural network NNsin.

The data of projections, for example a central pixel x and a predefined number of surrounding pixels/neighbours o of one projection represented as an image of intensities, is input to the first trained neural network NNsin. Based on the input data of projections, the first trained neural network NNsin automatically tunes the spatial projection filter parameter σs,sin and additionally or alternatively the intensity projection filter parameter σi,sin. In particular, the first neural network may output a value of one or both projection filter parameters or a respective change action (e.g. increase/decrease by X % [percent]) for the value of one or both projection filter parameters.

After automatic tuning of the projection filter parameter(s), each of the projections is filtered with the projection (J)BF F sin based on the respective projection filter parameters σs,sin/σi,sin. Thereby, each projection may be filtered using the same or different projection filter parameters. The projection (J)BF may be implemented on a projection filter module. The projection filter module may be a software module or a hardware module (e.g. data processing system, dedicated processing unit, etc.).

The filtered projections are backward-projected into a volume via the (W)FBP. Preferably, the FDK algorithm is used to back-project the volume from the filtered projections. The FDK algorithm is a widely used FBP algorithm for 3D image/volume reconstruction from cone-beam (CB) projections measured with a circular orbit of the x-ray scanner. A property of said algorithm is that the integral of the reconstructed image along any axial line orthogonal to the plane of the orbit is exact when the cone-beam projections are not truncated. The (W)FBP may be implemented on a backward-projection module. The backward-projection module may be a software module or a hardware module (e.g. data processing system, dedicated processing unit, etc.).

Alternatively, the FBP or fan beam scans or WFBP for helical cone beam scans can be used.

The data of the backward-projected volume is input to the second neural network NNvol.

The data of the backward-projected volume, for example a central voxel and a predefined number of surrounding voxels/neighbours o of the volume, is input to the second trained neural network NNvol. Based on the input data of the back-projected volume the second trained neural network NNvol automatically tunes the spatial volume filter parameter σs,vol and additionally or alternatively the intensity volume filter parameter σi,vol. In particular, the second trained neural network may output a value of one or both volume filter parameters or a respective change action (e.g. increase/decrease by X % [percent]) for the value of one or both volume filter parameters.

After automatic tuning of the volume filter parameter(s), the volume is filtered with the volume (J)BF Fvol based on the respective volume filter parameters σs,vol/σi,vol. Thereby, each voxel may be filtered using the same or different volume filter parameters. The volume (J)BF may be implemented on a volume filter module. The volume filter module may be a software module or a hardware module (e.g. data processing system, dedicated processing unit, etc.).

The filtered volume is either forward projected into projections, which are input to the first neural network NNsin for automatically tuning the projection filter parameter(s) in the next iteration, or output as final filtered i.e. reconstructed medical volume or images. In case the filtered volume does not meet the predefined quality criterion (e.g. predefined limit value for the Gradient Structural Similarity Index (GSSIM) or the like of the filtered image or predefined number of iterations), a further iteration is initiated by forwarding the filtered volume to the forward-projection, which may be implemented on a forward-projection module, and inputting the forward-projected projections to the first neural network NNsin. The forward-projection module may be a software module or a hardware module (e.g. data processing system, dedicated processing unit, etc.). In case the filtered volume meets the predefined quality criterion (e.g. predefined limit value for the GSSIM or the like of the filtered image), the filtered volume is output to an external output device like a monitor for a user (e.g. radiologist) as the reconstructed medical volume/images.

The first neural network NNsin and the second neural network NNvol have to be trained for automatically tuning the respective filter parameters of the two (J)BFs.

A learning or training rule/paradigm is an algorithm which modifies the parameters of a respective NN in order for a given input to the NN to produce a favoured output. This training typically amounts to modifying the weights and/or thresholds of the variables within the NN. Given a specific task to solve and a class of functions, learning/training device or apparatus using a set of observations (training input data of the training data) to find the one function of the class of functions, which solves the task in some optimal sense (corresponding labels or ground truth data of the training data). This entails defining a cost function or rather a loss function such that for the optimal solution the cost/loss is minimal and no other solution has a cost/loss less than the cost/loss of the optimal solution. The cost function or rather loss function is an important concept in learning/training, as it is a measure of how far away a particular solution is from an optimal solution to the problem to be solved. Learning/training algorithms search through the solution space to find a function that has the smallest possible cost/loss. For applications where the solution is data dependent, the cost/loss must necessarily be a function of the observations, otherwise the model would not relate to the data. It is frequently defined as a statistic to which only approximations can be made. It is possible to define an arbitrary cost function or rather loss function, however, a particular cost/loss function may be used either because it has desirable properties (e.g. convexity) or because it arises naturally from a particular formulation of the problem.

A NN can be discriminatively trained with a standard backpropagation algorithm. Backpropagation is a method to calculate the gradient of a loss function (produces the cost associated with a given state) with respect to the weights in the NN. The weight updates of backpropagation can be done via stochastic gradient descent. The choice of the loss function depends on factors such as the learning type (e.g. supervised, unsupervised, reinforcement etc.) and the activation function. Commonly, the activation function and loss function are the softmax function and cross-entropy function, respectively.

In other words, training a NN essentially means selecting one model from the set of allowed models (or, in a Bayesian framework, determining a distribution over the set of allowed models) that minimizes the cost or loss. Commonly some form of gradient descent is deployed, using backpropagation to compute the actual gradients. This is done by simply taking the derivative of the cost/loss function with respect to the network parameters and then changing those parameters in a gradient-related direction.

Backpropagation training algorithms fall into three categories: steepest descent (with variable learning rate and momentum, resilient backpropagation), quasi-Newton (Broyden-Fletcher-Goldfarb-Shanno, one step secant), Levenberg-Marquardt and conjugate gradient (Fletcher-Reeves update, Polak-Ribiére update, Powell-Beale restart, scaled conjugate gradient).

Common training paradigms include supervised learning, unsupervised learning and reinforcement learning. Supervised learning uses a set of example pairs and the aim is to find a function in the allowed class of functions that matches the examples. In other words, the mapping implied by the data is inferred; the cost/loss function is related to the mismatch between the mapping of the NN and the data and it implicitly contains prior knowledge about the problem domain. The cost/loss may be the mean-squared error, which tries to minimize the average squared error between the NN's output and a target value over all the example pairs. Minimizing this cost/loss using gradient descent for the class of NNs called multilayer perceptrons (MLP), produces the backpropagation algorithm for training NNs. In unsupervised learning, some data is given and the cost/loss function to be minimized that can be any function of the data and the NN's output. The cost/loss function is dependent on the task and any a priori assumptions (e.g. implicit properties or parameters of the model, observed variables etc.). In reinforcement learning, data is usually not given, but generated by an agent's interactions with the environment. At each point in time the agent performs an action and the environment generates an observation and an instantaneous cost or loss according to some (usually unknown) dynamics. The aim is to discover a policy for selecting actions that minimizes some measure of a long-term cost/loss, e.g. the expected cumulative cost/loss. The environment's dynamics and the long-term cost/loss for each policy are usually unknown, but may also be estimated. The environment is commonly modelled as a Markov decision process (MDP) with states and actions with the following probability distributions: the instantaneous cost distribution, the observation distribution and the transition, while a policy is defined as the conditional distribution over actions given the observations. Taken together, the two then define a Markov chain (MC). The aim is to discover the policy (i.e., the MC) that minimizes the cost/loss.

The goal of training a NN is to optimize the weights and optionally other parameters of the NN such that the NN correctly maps input data provided at its input or rather input node(s) to output data at its output or rather output node(s). First, input data (one randomly selected sample of the training data set) is forward-propagated through the NN by providing the input data at the input of the NN. As a result of the forward-propagation a current output is computed by the NN based on the input data provided to the input node(s) and the internal weights of the NN. The current output is provided at the output node(s) of the NN. Then the current output is compared to the label or ground truth data of the training data set that is associated with the (randomly selected) input data. The comparison can be done by an error function or cost/loss function that computes an error/cost/loss. In order to archive training or learning the error/cost/loss is back-propagated by adapting the weights of the NN based on the computed error/cost/loss.

According to one or more example embodiments, both neural networks are trained back to back/jointly using a reinforcement learning algorithm.

Firstly, a training set is provided. The training set comprises training data of a predefined number of training volumes. For example, the AAMP Low Dose CT Grand Challenge dataset (C. H. Mccollough, "Low Dose CT Grand Challenge", 2016) may be used for training the first and second neural networks. The training data of training volumes comprises corresponding data of respective projections.

Secondly, the (untrained) first neural network NNsin and the second neural network NNvol are provided. The two neural networks may be implemented on a common or each on a separate (training) machine learning module. The (training) machine learning module(s) may be a software module or a hardware module (e.g. data processing system, dedicated processing unit, etc.).

The first neural network NNsin is configured to receive data of projections as input, for example at an input layer. The data of projections may each comprise one central pixel and the predefined number of neighbours o of the central pixel x of one projection. The projections used for training may be forward projected from the received training volumes or be comprised in the training set. The first neural network NNsin is further configured to provide the spatial projection filter parameter σs,sin and additionally or alternatively the intensity projection filter parameter σi,sin of the projection (J)BF F sin as output, for example at an output layer. Between the input layer and the output layer at least one layer comprising at least two nodes may be comprised.

Likewise, the second neural network NNvol is configured to receive data of a volume as input, for example at an input layer. The data of the volume may comprise at least a part or all voxels of the volume each represented as central voxel together with the predefined number of neighbours o. The second neural network NNvol is further configured to provide the spatial volume filter parameter σs,vol and additionally or alternatively the intensity volume filter parameter σi,vol of the volume (J)BF Fvol as output, for example at an output layer. Between the input layer and the output layer at least one layer comprising at least two nodes may be comprised.

Afterwards, the first and second neural network are trained, in particular back to back/jointly, each based on a respective reward. Thereto a reinforcement learning algorithm may be used. The reward may, for example, be derived from comparing the quality of a projection or rather volume filtered with the current filter parameters with the quality of a precedingly filtered projection/volume. The weights of both neural networks are iteratively adjusted based on the respective reward until a predefined break criterion, for example a predefined number of iterations or a minimal difference between the weights of the current iteration and the weights of the preceding iteration, and the like, is met.

The reward may be calculated based on comparing the current filtered projections with previous filtered projections or with ground truth (i.e.) projections comprised by the training set and, accordingly, based on comparing the current filtered volume with a previous filtered volume or a ground truth (i.e. ideal) volume comprised by the training set.

In particular, a Q-learning approach, a policy gradient or A3C approach may be used for training the first and second neural network.

The trained first and second neural network, according to one or more example embodiments, replace a human operator for tuning the filter parameters of the two (J)BFs in the projection/projection domain and the volume/image domain, respectively.

With the reconstruction, according to one or more example embodiments, using the trained first and second neural networks to automatically tune the filter parameters of the two (J)BFs for filtering the projections/projections as well as the volume, artefacts in the medical volume or rather medical images can be significantly reduced and the image quality, thus, further improved. At the same time, the time for tuning the filter parameters is reduced and interpretability of the whole process nevertheless given, i.e. the iterative automatic tuning of the filter parameters via the first and second neural network is retraceable (no black-box).

According to a refinement of one or more example embodiments, the spatial projection filter parameter σs,sin and the intensity projection filter parameter σi,sin are tuned for each of the projections, in the step d).

Likewise, in training the first neural network NNsin more than one projection forward projected from the same training volume are used to train the first neural network NNsin for automatically tuning the spatial projection filter parameter σs,sin and additionally or alternatively the intensity projection filter parameter σi,sin.

Instead of using one pair of projection filter parameters for filtering all projections, a respective pair (or one of the respective pair) of projection filter parameters is automatically tuned for filtering each of the received projections. Since noise in the projection domain follows a Poisson distribution, global filter parameters for each projection are sufficient to remove the noise. Therefore, only an optimal set of filter parameters for each of the received projections needs to be automatically tuned, instead of for each pixel of each received projection.

Thus, the computation time is significantly reduced, while the quality of the reconstructed medical volume/images is not significantly reduced.

According to a refinement of one or more example embodiments, the spatial volume filter parameter σs,vol and additionally or alternatively the intensity volume filter parameter σi,vol are tuned for each voxel of the volume, in step h).

Likewise, in training the second neural network NNsin more than one voxel of the volume used for training is used to train the second neural network NNvol for automatically tuning the spatial volume filter parameter σs,vol and additionally or alternatively the intensity volume filter parameter σi,vol.

The noise in the volume/image domain is non-linear and, consequently, the two volume filter parameters are automatically tuned for each voxel of the volume instead of using only one global set of volume filter parameters for the whole volume.

Thus, the quality of the reconstructed medical volume/images is further increased.

According to a refinement of one or more example embodiments, the first neural network NNsin and additionally or alternatively the second neural network NNvol are convolutional neural networks (CNN).

CNN is a class of deep neural networks, most commonly applied in analysing images. In CNNs weights are shared in the architecture and they have translation invariance characteristics. CNNs are regularized versions of multilayer perceptrons (fully connected networks). Each neuron in one layer is connected to all neurons in the next layer. For regularization (to avoid over-fitting) CNNs take advantage of the hierarchical pattern in data and assemble more complex patterns using smaller and simpler patterns. Therefore, on the scale of connectedness and complexity, CNNs are on the lower extreme. CNNs use relatively little pre-processing compared to other classification algorithms. This means that the network learns the filters that in traditional algorithms were hand-engineered. This independence from prior knowledge and human effort in feature design is a major advantage.

The first neural network NNsin for filtering the projections may in particular be a 2D CNN. The input of 2D CNNs is a matrix (2 directions, e.g. (x,y)) of a given size (e.g. W×H) to calculate using a filter of a given size (e.g. k×k) the convolution output-shape as matrix of the same or a different given size (e.g. W×H) (e.g. Sobel Egde Fllter).

The second neural network NNvol may in particular be a 3D CNN. The input of 3D CNNs is a volume/3D tensor (3 directions, e.g. (x,y,z)) of a given size (e.g. W×H×L) to calculate using a filter of a given size (e.g. k×k×d, where d<L) the convolution output-shape as volume/tensor of the same or a different given size (e.g. W×H×L) (e.g. C3D).

The first neural network NNsin is a first (2D) convolutional neural network CNNsin. Additionally or alternatively, the second neural network NNvol is a second (3D) convolutional neural network CNNvol. Both convolutional neural networks may each comprise an input layer, several filter layers, a condensation layer, and an output layer. The input layer of the first neural network NNsin may be configured to receive a central pixel x with neighbours o of a projection, for example the input layer may be configured to receive 5×5 pixels (1 central pixel x and 24 neighbours o) of a projection. The input layer of the second neural network NNvol may be configured to receive a central voxel x with neighbours o of a volume, for example the input layer may be configured to receive 5×5×5 voxel (1 central voxel x and 124 neighbours o) of a volume.

The first and additionally or alternatively the second neural network may comprise a bifurcation into two branches. For example the first or second neural network may comprise:
  a first layer of 32 (2D/3D) filters subsequent to the input layer, wherein each filter reduces the size of the input;
  a second layer of 64 (2D/3D) filters subsequent to the first layer, wherein each filter reduces the size of the input;
  a parameter branch subsequent to the second layer comprising:
  a first parameter layer of 64 (2D/3D) filters, wherein each filter reduces the size of the input;
  a parameter condensation layer of 128 nodes;
  a parameter output layer of two nodes, one node for each of the two filter parameters;
  an action branch subsequent to the second layer comprising:
  a first action layer of 128 (2D/3D) filters, wherein each filter reduces the size of the input;

a second action layer of 128 (2D/3D) filters;
an action condensation layer of 256 nodes; and
an action output layer of five nodes, one node for each possible change action to the filter parameter.

The number of filters in each layer according to an advantageous example may be adapted depending, e.g., on the datasate or the like. The utilization of convolutional neural network(s) enables particular precise and fast automatic tuning of the filter parameters.

According to a refinement of one or more example embodiments, at least one of the group comprising the first neural network NNsin and the second neural network NNvol is configured to automatically select one of the respective spatial filter parameter σs,sin/σs,vol and intensity filter parameter σi,sin/σi,vol, respectively, to be tuned.

The first neural network NNsin and additionally or alternatively the second neural network NNvol selects one of the respective two filter parameters to be automatically tuned. Consequently, in each iteration only one of the two filter parameters for one or both of the projection (J)BF and the volume (J)BF is automatically tuned.

For example, via the parameter branch of the respective neural network the one parameter of the spatial projection/volume filter parameter and the intensity projection/volume filter parameter, whose change will contribute most to denoising the received projection/volume, is chosen for automatic tuning.

Thereby, the amount of iterations and, thus, time needed to automatically tune the filter parameters is further reduced.

According to a refinement of one or more example embodiments, at least one of the group comprising the first neural network NNsin and the second neural network NNvol is configured to output one of a predefined number of actions to tune the respective filter parameter(s) σs,sin/σs,vol/σi,sin/σi,vol.

The first neural network NNsin and additionally or alternatively the second neural network NNvol selects one action of the predefined number of actions to tune the (selected) filter parameter(s). Consequently, in each iteration the one selected filter parameter or both filter parameters of the projection (J)BF and additionally or alternatively the volume (J)BF is automatically tuned by applying one specific action of tuning (e.g. increase parameter value by 10% [percent]).

For example, via the action branch of the respective neural network the one action of the predefined number of actions to change the (selected) filter parameter(s), whose change will contribute most to denoising the received projection/volume, is chosen for automatic tuning.

Thereby, the amount of iterations and, thus, time needed to automatically tune the filter parameters is further reduced.

According to a further refinement of one or more example embodiments, the predefined number of actions to tune the respective filter parameter(s) σs,sin/σs,vol/σi,sin/σi,vol comprise "increase parameter value by 50%"; "increase parameter value by 10%"; "do not change parameter value"; "decrease parameter value by 10%"; and "decrease parameter value by 50%".

With these five predefined actions to change the respective (selected) filter parameter(s), the amount of iterations and, thus, time needed to automatically tune the filter parameters is even further reduced.

According to a refinement of one or more example embodiments, the step t4) of training the first neural network NNsin and the second neural network NNvol comprises the following sub-steps:

t4.1) Randomly selecting one or more of the training volumes and either selecting training projections comprised in the corresponding training data or forward-projecting projections from the selected training volume as current projections; and for each selected training volume:

t4.2) Filtering the current projections with the projection (J)BF F sin based on the projection filter parameters σs,sin, σi,sin tuned by the first neural network NNsin based on current weights of the first neural network Nnsin;

t4.3) Updating weights of the first neural network NNsin based on the reward estimated from a volume backward-projected from the filtered projections and a volume backward-projected based on the current projections and, in case a predefined first stop criterion is not met, forwarding the filtered projections as current projections and returning to SUB-step t4.2);

t4.4) Forwarding the volume backward-projected from the filtered projections as current volume;

t4.5) Filtering the current volume with the volume (J)BF Fvol based on the volume filter parameters σs,vol, σi,vol tuned by the second neural network NNvol based on current weights of the second neural network Nnvol;

t4.6) Updating weights of the second neural network NNvol based on the reward estimated from the filtered volume and the current volume and, in case a predefined second stop criterion is not met, forwarding the filtered volume as current volume and returning to sub-step t4.5).

The first neural network NNsin for projection filter parameter tuning may be trained with the similarity of the simulated projections to the collected data as a reward function. The second neural network NNvol for volume filter parameter tuning network may be trained using a reward network which calculates the noise content of the image as well as simulating an anthropomorphic model observer.

One or more training volumes or rather the corresponding training data are randomly selected from the training set. For each of the one or more selected training volumes the training steps t4.1) to 4.6) are executed in order to train the first neural network NNsin and the second neural network NNvol.

In case the training data comprised in the training set includes the corresponding training projections for each of the training volumes, the training projections pertaining to the respective randomly selected one or more training volumes are forwarded as the current projections for the first iteration. In case the training data comprised in the training set does not include training projections, projections are forward-projected from the selected one or more training volume(s) as the current projections for the first iteration.

The sub-steps t4.2) and t4.3) are iteratively executed for tuning the first neural network NNsin until the first stop criterion is met (e.g. predefined number of iterations, value of a quality measure, difference between current filtered and previous projection/volume).

The current projections are filtered with the projection (J)BF F sin using the current projection filter parameters σs,sin, σi,sin. In the first iteration, the projection filter parameters σs,sin, σi,sin are set to a predefined value or have a value tuned for a previously selected training volume. In each subsequent iteration, the projection filter parameters σs,sin, σi,sin have a value tuned by the first neural network NNsin in the preceding iteration. Thereby, the tuning of the projection filter parameters σs,sin, σi,sin in the previous iteration is based on the current (updated in the preceding iteration) weights of the first neural network NNsin.

For updating the weights of the first neural network NNsin the corresponding reward is estimated. The reward is estimated or calculated by comparing the volume backward-projected (e.g. (W)FBP) from the filtered projections with the volume backward-projected (e.g. (W)FBP) from the current projections. Based on the estimated reward, the weights of the first neural Network NNsin are adjusted. In case the first stop criterion is not met, the filtered projections are forwarded as the current projections and a new iteration at sub-step t4.2) is started.

In case the first stop criterion is met, the volume backward-projected from the filtered projections is forwarded as the current volume and the training is continued at sub-step t4.5).

The sub-steps t4.5) and t4.6) are iteratively executed for tuning the second neural network NNvol until the second stop criterion is met (e.g. predefined number of iterations, value of a quality measure, difference between current filtered and previous projection/volume).

The current volume is filtered with the volume (J)BF Fvol using the current volume filter parameters σs,vol, σi,vol. In the first iteration, the volume filter parameters σs,vol, σi,vol are set to a predefined value or have a value tuned for a previously selected training volume. In each subsequent iteration, the volume filter parameters σs,vol, σi,vol have a value tuned by the second neural network NNvol in the preceding iteration. Thereby, the tuning of the volume filter parameters σs,vol, σi,vol in the previous iteration is based on the current (updated in the preceding iteration) weights of the second neural network NNvol.

For updating the weights of the second neural network NNvol the corresponding reward is estimated. The reward is estimated or calculated by comparing the filtered volume with the current volume. Based on the estimated reward, the weights of the second neural Network NNvol are adjusted. In case the second stop criterion is not met, the filtered volume is forwarded as the current volume and a new iteration at sub-step t4.5) is started.

In case the second stop criterion is met, the training of the first and second neural network based on the current selected training volume is stopped. In case, there have been randomly selected more than one training volumes for training the two neural networks, the training is continued at sub-step 4.2) with the training data of the next randomly selected training volume.

Preferably, the first and second stop criterion may each be a predefined number of iterations.

With the reward-based training of the first and second neural network, the time for training both neural networks is significantly reduced.

According to a refinement of one or more example embodiments, the first neural network NNsin is trained by a Q-learning approach based on the reward estimated using a reward network Nrew. The weights of the first neural network NNsin are updated based on the reward estimated from the backward-projected filtered projections and backward-projected current projections using the reward network Nrew. Additionally or alternatively, The second neural network NNvol is trained by a Q-learning approach based on the reward estimated using the reward network Nrew. The weights of the second neural network NNvol are updated based on the reward estimated from the filtered volume and current volume using the reward network Nrew.

Q-learning approaches or algorithms are reinforcement learning approaches/algorithms to learn quality of actions telling an agent what action to take under what circumstances. For any finite Markov decision process (FMDP, mathematical framework for modelling decision making in situations where outcomes are partly random and partly under the control of a decision maker) Q-learning approaches/algorithms find an optimal policy in the sense of maximizing the expected value of the total reward over any and all successive steps, starting from the current state. Q-learning algorithms can identify an optimal action-selection policy for any given FMDP, given infinite exploration time and a partly-random policy. "Q" names the function that the algorithm computes with the maximum expected rewards for an action taken in a given state.

To achieve improved image quality based on the automatically tuned filter parameters, a policy has to be learned, which tunes the filter parameters such as to create an optimal image. This policy is learned via the Q-learning approach, defined by the following equation:

$$Q^*(s, a) = \max_\pi [r^k + \gamma r^{k+1} + \gamma^2 r^{k+2} + \ldots \mid s_k = s, a_k = a, \pi],$$

where Q* is the optimal action value to be achieved, n is the action choosing policy, s is the current state, and a is the action chosen at state s. a is defined as a function of parameter p and tuning strength t.

A property of Q*(s,a) (as described in Bellman, "Dynamic Programming," Science, vol. 153, no. 3731, pp. 34-37, 1966) is the following:

$$Q^*(s, a) = r + \gamma \cdot \max_a Q^*(s', a'),$$

where r is the reward achieved by the optimal action a at s. s' is the state observed when a is taken at s. The value action function is parametrised with weights W, which can be determined by penalizing the deviation from the Bellman equation above. This deviation is represented by the following equation for the loss L:

$$L(W) = \left[ r + \gamma \cdot \max_a Q(s', a'; W) - Q(s, a; W) \right]^2$$

Then, a new variable W' is introduced, which represents an older version of the weights. Further, double deep-Q-learning may be introduced to prevent overestimations the neural networks. The loss L is then defined as:

$$L(W) = \left[ r + \gamma Q\left(s', Q \max_{a'} Q(s', a'; W); W'\right) - Q(s, a; W) \right]^2$$

As described further above, the first neural network NNsin and additionally or alternatively the second neural network NNvol may have two paths, one path to choose the filter parameter to be tuned, and another path to select an action to tune it. Therefore, the above loss function is split into two parts to train the two neural networks given as:

$$L(W) = \left[ 2r + \gamma Q\left(s', Q \max_{p'} Q(s', p'; W); W'\right) + \right.$$
$$\left. \gamma Q\left(s', Q \max_{t'} Q(s', t'; W); W'\right) - (Q(s, p; W) + Q(s, t; W)) \right]^2,$$

where p, p' and t, t' represent the path for parameter selection and action selection, respectively.

With the Q-learning approach both neural networks are trained even more efficiently.

According to a further refinement of one or more example embodiments, the reward network Nrew is a neural network trained to predict a quality score IRQM for estimating the reward.

A neural network, in particular a convolutional neural network, is utilized to predict the quality score IRQM, which is based on the GSSIM, from current (noisy) volumes/images without having to compare the latter to a reference (e.g noise-free volume/image). The reward (convolutional) neural network may include four convolutional layers with 3×3 kernels, followed by a global average pooling layer and a fully connected layer. The convolutional layers may contain 16, 16, 32, and 32 filters. The fully connected layer may contain 32 neurons. Each layer may be followed by an eLU activation layer.

The target for training the reward network to predict the quality score IRQM from current (noisy) volumes or images can, for example, be represented by the following equation:

$$T(IM_1) = GSSIM(IM_1, IM_2) + \frac{1}{\frac{\text{mean}\left((IM_1 - IM_2)^2\right)}{ROI} + 1}$$

where IM1 is the current (noisy) volume/image, IM2 is the clean (noise-free) volume/image, and GSSIM is the gradient structural similarity metric. The second term attempts to measure the noise power in the volume. ROI is the receptive field of the network (e.g. 9×9). The reward network Nrew may have been trained on a subset of five patients reconstructed at standard, 50%, and 25% dose. The dataset may be augmented by flips, rotations, and Gaussian blurs. Random patches of size 32, 48, 64, and 96 may have been extracted for training the reward network Nrew. Optimization may have been performed using the Adam optimizer (D. P. Kingma and J. L. Bai, "Adam: A Method for Stochastic Optimization," in International Conference on Learning Representations, 2015) with a learning rate of 1×10-4 over 30 epochs.

Using the above described (convolutional) neural network as the reward network Nrew is particularly efficient for training.

BRIEF DESCRIPTION OF THE DRAWINGS

The present invention and its technical field are subsequently explained in further detail by (an) exemplary or example embodiment(s) shown in the drawing(s). The exemplary (or example) embodiment(s) only conduce(s) better understanding of the present invention and in no case is/are to be construed as limiting for the scope of the present invention. Particularly, it is possible to extract aspects of the subject-matter described in the figure(s) and to combine it with other components and findings of the present description or figure(s), if not explicitly described differently. Equal reference signs refer to the same objects, such that explanations from other figures may be supplementally used.

FIG. 12 is a schematic view of the architecture of the convolutional neural network used as reward network Nrew.

DETAILED DESCRIPTION

Figure 1:
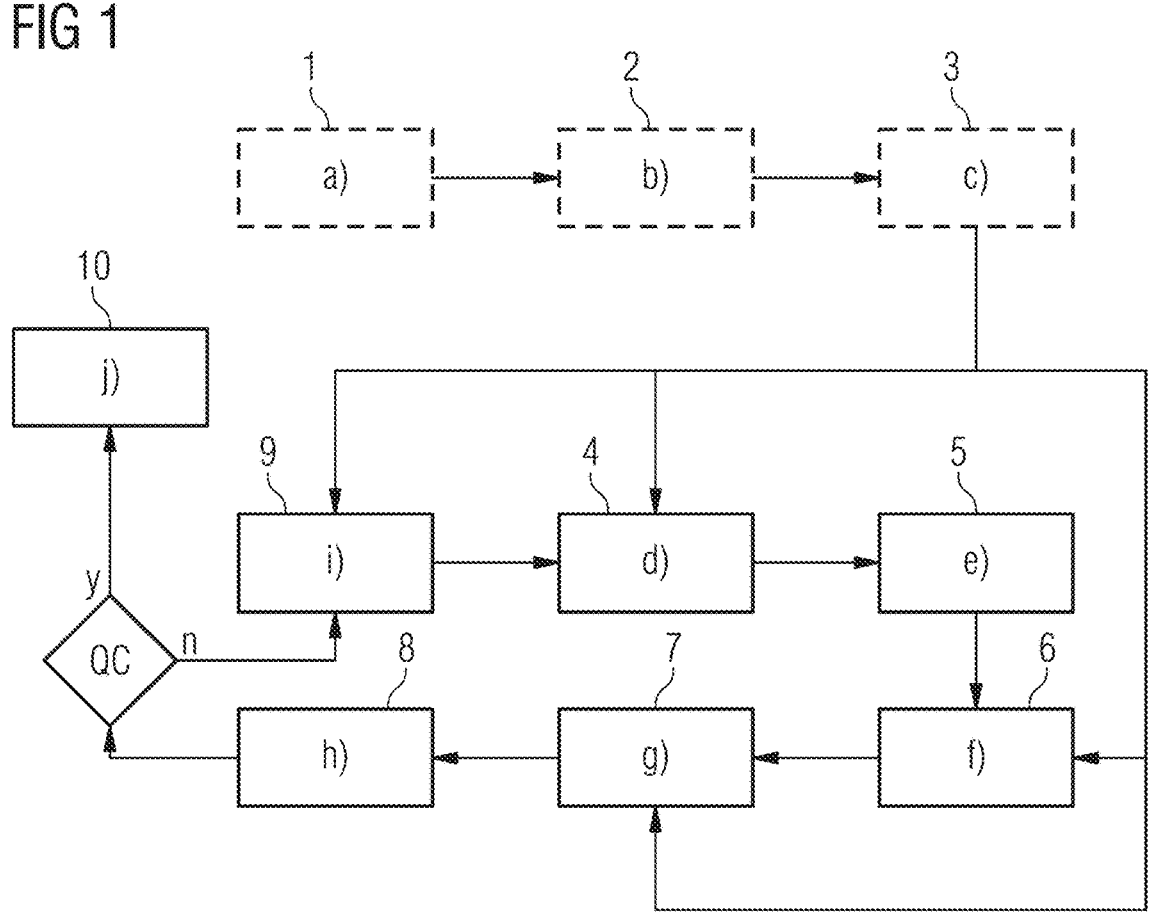
FIG. 1 is a schematic flow chart of the method of iteratively reconstructing medical images or a medical volume using deep learning and of the computer-program according to the second aspect of example embodiments.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one example embodiment, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/ DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one example embodiment provides a method (or improved method) of iteratively reconstructing images using deep learning as well as a corresponding improved computer program, a corresponding improved non-transitory computer-readable medium and/or a corresponding improved data processing system.

According to a first aspect of example embodiments, a computer-implemented method of iteratively reconstructing images or a volume, in particular medical images or a medical volume like computer tomography (CT) images or a CT volume, using deep learning, comprises the following steps:

d) Automatically tuning a spatial projection filter parameter σs,sin and additionally or alternatively an intensity projection filter parameter σi,sin of a projection (joint) bilateral filter ((J)BF), i.e. a projection bilateral filter (BF) or a projection joint bilateral filter (JBF), F sin by a first trained neural network NNsin based on data of projections, in particular sinograms, of an imaging procedure, in particular a medical (CT) scan, in case the first iteration starts at step i), or on data of forward projected projections, otherwise;

e) Filtering the projections with the projection (J)BF F sin using the respective automatically tuned projection filter parameters σs,sin/σi,sin;

f) Backward-projecting a volume from the projections of the imaging procedure, in particular the medical (CT) scan, in case the first iteration starts at step f), or from the filtered projections, otherwise, using a (weighted) filtered back-projection ((W)FBP), in particular the algorithm of Feldkamp, Davis and Kress (FDK), the FBP algorithm or the WFBP algorithm;

g) Automatically tuning a spatial volume filter parameter σs,vol and additionally or alternatively an intensity volume filter parameter σi,vol of a volume (J)BF, i.e. a volume BF or a volume JBF, Fvol by a second trained neural network NNvol based on data of a volume of the imaging procedure, in particular a medical (CT) scan, in case the first iteration starts at step g), or on the backward-projected volume, otherwise;

h) Filtering the volume with the volume (J)BF Fvol using the respective automatically tuned volume filter parameters σs,vol/σi,vol;

i) Forward-projecting projections from the volume of the imaging procedure, in particular a medical (CT) scan, in case the first iteration starts at step i), or from the filtered volume and returning to step d), in case the filtered volume does not meet a predefined quality criterion, otherwise; and j) Outputting the filtered volume as the reconstructed medical images or volume, in particular as the reconstructed CT images or volume, in case the filtered volume meets the predefined quality criterion.

The first iteration starts at one of the group comprising step d); step f); step g) and step i).

According to a second aspect of example embodiments, a computer program product comprises instructions which, when executed on a data processing system, cause the system to execute the steps of the method according to the first aspect of example embodiments.

According to a third aspect of example embodiments, a computer-readable medium comprises the computer program product according to the second aspect of example embodiments.

According to a fourth aspect of example embodiments, a data processing system for iteratively reconstructing medical images or a medical volume using deep learning, that is in particular configured to execute the steps of the method according to the first aspect of example embodiments, comprises an input module configured to receive projections and/or volumes of a imaging procedure, in particular a medical (CT) scan; an output module configured to be communicatively connected with and to provide volumes to external modules; a projection (joint) bilateral filter ((J)BF), i.e. a projection bilateral filter (BF) or a projection joint bilateral filter JBF, F sin; a volume (J)BF, i.e. a volume BF or a volume JBF, Fvol; a backward-projector; a forward-projector; a first trained neural network NNsin; and a second trained neural network NNvol. The projection (J)BF F sin is configured to filter projections. The volume (J)BF Fvol is configured to filter volumes. The backward-projector is communicatively connected to the (J)BF F sin and configured to backward-project volumes from projections. The forward-projector is communicatively connected to the volume (J)BF Fvol and configured to forward-project projections from volumes. The first trained neural network NNsin is communicatively connected to the forward-projector and configured to receive data of projections as input and to provide a spatial projection filter parameter σs,sin and additionally or alternatively an intensity projection filter parameter σi,sin of the projection (J)BF F sin as output. The second trained neural network NNvol is communicatively connected to the backward-projector and configured to receive data of a volume as input and to provide a spatial volume filter parameter σs,vol and additionally or alternatively an intensity volume filter parameter σi,vol of the volume (J)BF Fvol as output. The input module is communicatively connected to at least one of the group comprising first trained neural network NNsin; the second trained neural network NNvol; the backward-projector; and/or the forward-projector. The first trained neural network NNsin is configured to automatically tune the spatial projection filter parameter σs,sin and additionally or alternatively the intensity projection filter parameter σi,sin of a of the (J)BF F sin based on data of the projections of the imaging procedure, in particular a medical (CT) scan, or on data of the forward projected projections. The projection (J)BF F sin is configured to filter the projections using the respective automatically tuned projection filter parameter(s) σs,sin/σi,sin. The backward-projector is configured to backward-project a volume from the projections of the imaging procedure, in particular a medical (CT) scan, or from the filtered projections using a (weighted) filtered back-projection ((W)FBP). The second trained neural network NNvol is configured to automatically tune the spatial volume filter parameter σs,vol and additionally or alternatively the intensity volume filter parameter σi,vol of the volume (J)BF Fvol based on the received data of the volume of the imaging procedure, in particular a medical (CT) scan, or on the backward-projected volume. The volume (J)BF is configured to filter the volume using the respective automatically tuned volume filter parameter(s) σs,vol/σi,vol. The forward-projector is configured to forward-project projections from the volume of the imaging procedure, in particular a medical (CT) scan, or from the filtered volume. The output module is communicatively connected to the volume (J)BF Fvol and configured to provide the filtered volume to external modules, in case the filtered volume meets a predefined quality criterion.

According to a fifth aspect of example embodiments a CT system comprises a CT scanner; the data processing system according to the fourth aspect of example embodiments; and an output device. The data processing system is communicatively connected to a controller of the CT scanner or integrated in the controller of the CT scanner. The output device is communicatively connected to the data processing system. The data processing system is configured to receive data of projections and additionally or alternatively of volumes of CT scans conducted by the CT scanner via the input module of the data processing system as input. The data processing system is further configured to provide filtered volumes to the output device via the output module of the data processing system.

According to a sixth aspect of example embodiments, a computer-implemented method of training a first neural network NNsin for automatically tuning a projection filter parameter σs,sin/σi,sin for a projection (joint) bilateral filter ((J)BF) F sin for projections and a second neural network NNvol for automatically tuning a volume filter parameter σs,vol/σi,vol for a volume (J)BF Fvol for volumes comprises the following steps:
  t1) Providing a training set comprising training data of training volumes, in particular CT training volumes;
  t2) Providing a first neural network NNsin configured to receive data of projections as input and to provide a spatial projection filter parameter σs,sin and additionally or alternatively an intensity projection filter parameter σi,sin of a projection (J)BF F sin as output;
  t3) Providing a second neural network NNvol configured to receive data of a volume as input and to provide a spatial volume filter parameter σs,vol and additionally or alternatively an intensity volume filter parameter σi,vol of a volume (J)BF Fvol as output; and
  t4) Training the first neural network NNsin and the second neural network NNvol based on a respective reward for each of the first and second neural network;

According to a seventh aspect of example embodiments, a computer program product comprises instructions which, when executed on a data processing system, cause the system to execute the steps of a method according to the sixth aspect of example embodiments.

According to an eighth aspect of example embodiments a computer-readable medium comprises the computer program product according to the seventh aspect of example embodiments.

According to a ninth aspect of example embodiments, a data processing system comprises one or more processors or other processing circuitry configured to execute the steps of a method according to the sixth aspect of example embodiments.

According to one or more example embodiments, medical images or a medical volume, in particular CT images or a CT volume, is iteratively reconstructed using (weighted) filtered back-projection ((W)FBP). The quality of the reconstructed images or volume is improved by using deep learning in both the projection (raw data or projection) domain and volume (image) domain. This deep iterative reconstruction may utilize reinforcement learning to train the respective neural networks to tune filter parameters within both the projection domain and the volume domain.

The iterative reconstruction of medical images or a medical volume, according to one or more example embodiments, involves a reconstruction technique which functions in a single pass, eg. (W)FBP, and a simple forward projector to generate projections (projections).

The steps d) to i) are executed iteratively until the filtered volume meets the predefined quality criterion. The first iteration of steps d) to i) can start at step d), step f), step g) or step i).

A method according to the first aspect of example embodiments, may further comprise the following (non-iterative) steps before the iterative steps d) to i):
  a) Providing the first trained neural network NNsin configured to receive data of projections as input and to provide a spatial projection filter parameter σs,sin and additionally or alternatively an intensity projection filter parameter σi,sin of the projection (J)BF F sin as output;
  b) Providing the second trained neural network NNsin configured to receive data of a volume as input and to provide a spatial volume filter parameter σs,vol and additionally or alternatively an intensity volume filter parameter σi,vol of the volume (J)BF Fvol as output; and
  c) Receiving data of the projections and additionally or alternatively data of the volume of the imaging procedure, in particular a medical (CT) scan.

Firstly, the first trained neural network NNsin for tuning the projection filter parameters and the second trained neural network NNvol for tuning the volume filter parameters may be provided (steps a) and b)). The first and second neural network may be implemented on a common or each on a separate machine learning module. The machine learning module(s) may be a software module or a hardware module (e.g. data processing system, dedicated processing unit, etc.).

The first neural network NNsin is trained to automatically tune the spatial projection filter parameter σs,sin and additionally or alternatively the intensity projection filter parameter σi,sin of the projection (J)BF F sin for filtering the projections (of the imaging procedure, in particular a medical (CT) scan, or forward-projected from a volume e.g. of the same or a previous iteration).

The second neural network NNvol is trained to automatically tune the spatial volume filter parameter σs,vol and additionally or alternatively the intensity volume filter parameter σi,vol of the volume (J)BF Fvol for filtering the volume (of the imaging procedure, in particular a medical (CT) scan, or backward-projected from projections e.g. of the same or a previous iteration).

The projection and volume (J)BF are both (J)BFs. A BF is a non-linear filter combining a spatial smoothing filter c and an intensity filter s. The spatial filter c is based on a closeness function which accounts for spatial distance between a central pixel/voxel x and its neighbours o:

$$c(x, o) = G_{\sigma_s}(x - o) = \frac{1}{\sqrt{2\pi}\,\sigma_s} e^{-\left(\frac{(d(x,o))^2}{2\sigma_s^2}\right)},$$

$$d(x, o) = \|x - o\| = \sqrt{(x_1 - o_1)^2 + (x_2 - o_2)^2 + (x_3 - o_3)^2},$$

where σs is the amount of spatial smoothing and d(x,o) is the distance between pixel/voxel x and its neighbour o. The intensity filter s based on a similarity function between intensities I of the central pixel/voxel x and its neighbours o:

$$s(x, o) = G_{\sigma_i}(I(x) - I(o)) = \frac{1}{\sqrt{2\pi}\,\sigma_i} e^{-\left(\frac{(\delta(I(x),I(o)))^2}{2\sigma_i^2}\right)},$$

$$\delta(I(x), I(o)) = \|I(x) - I(o)\|,$$

where σi is the amount of intensity smoothing and δ is the difference between the intensities I of the central pixel/voxel x and its neighbour o. In both filters, the constant $\sqrt{2\pi}$ may be omitted as it would be compensated during training of the first and second neural network. The volume or rather the projection FT filtered with the BF is calculated via the following equation:

$$FT(x) = \frac{\sum_{o \in N(x)} IN(o) G_{\sigma_s}(x - o) G_{\sigma_i}(I(x) - I(o))}{\sum_{o \in N(x)} G_{\sigma_s}(x - o) G_{\sigma_i}(I(x) - I(o))},$$

where IN is the input (i.e. noisy) volume or rather projection and N(x) is the considered neighbourhood of the central pixel/voxel x. The BF reduces noise and preserves edges. A JBF has the same structure as a BF and additionally uses a deep learned guidance image to further denoise the image/volume or projection. The volume or rather the projection FT filtered with the JBF is calculated via the following equation:

$$FT(x) = \frac{\sum_{o \in N(x)} IN(o) G_{\sigma_s}(x - o) G_{\sigma_i}(I_g(x) - I_g(o))}{\sum_{o \in N(x)} G_{\sigma_s}(x - o) G_{\sigma_i}(I_g(x) - I_g(o))},$$

where Ig is the intensity in the guidance image (projection or volume).

The filter for the projection F sin, according to one or more example embodiments, is a BF or a JBF. The filter for the volume Fvol, according to one or more example embodiments, is a BF or a JBF.

The first and second neural network for automatically tuning the projection and volume filter parameters of the respective (J)BFs may comprise an input layer configured to receive data of projections or rather of a volume. The first and second neural network may further comprise an output layer configured to output a value of one or of each filter parameter or rather a change action for one or for each filter parameter. Between the input and output layer the first and second neural network may comprise at least one layer comprising at least two neurons.

Artificial neural networks (ANN) or short neural networks (NN) are systems, in particular computing systems, inspired by biological neural networks that constitute animal brains. NNs "learn" to perform tasks by considering (labelled) examples called training data, generally without being designed with any task-specific rules. During an initial learning or training phase NNs automatically generate identifying characteristics from the (labelled) training data. NNs comprise a collection of connected nodes called artificial neurons, which loosely model the neurons in a biological brain. Each connection (synapses in the biological brain) can transmit a signal from one node to another. A node that receives a signal can process it and then signal to subsequent neurons connected to it. In common NN implementations, the signal at a connection between nodes is a real number (e.g. 0 . . . 1), and the output of each artificial neuron is computed by some non-linear function of the sum of its inputs (from other nodes). The connections between nodes are called "edges". The edges in NNs may each have a weight that is adjusted during training of the NNs. The weight increases or decreases the strength of the signal at the corresponding edge. Nodes may each have a threshold such that the signal is only sent if an aggregate signal exceeds that threshold. Typically, nodes are aggregated into layers. Different layers may perform different kinds of transformations on their inputs. Signals travel from a first layer or input layer to a last layer or output layer, possibly after traversing the layers multiple times.

In other words, an NN is a network of simple elements, the so-called nodes or artificial neurons, which receive input. After receiving input the nodes change their internal state (activation) according to that input, and produce output depending on the input and activation. The network forms by connecting the output of certain nodes to the input of other nodes forming a directed, weighted graph. The weights as well as the functions that compute the activation of each node can be modified during initial learning/training, which is governed by a learning rule or paradigm.

A node/neuron receiving an input from at least one predecessor node/neuron consists of the following components: an activation, the node's state, depending on a discrete time parameter, optionally a threshold, which stays fixed unless changed by a learning/training function, an activation function (e.g. hyperbolic tangent function, sigmoid function, softmax function, rectifier function etc.) that computes the new activation at a given time and the net input and an output function computing the output from the activation (often the output function is the identity function). An important characteristic of the activation function is that it provides a smooth transition as input values change, i.e. a small change in input produces a small change in output.

An input node has no predecessor but serves as input interface for the whole NN. Similarly an output node has no successor and thus serves as output interface of the whole NN. An NN consists of edges/connections, each edge transferring the output of a node (predecessor) to the input of another, succeeding node (successor). Additionally to the assigned weight an edge may have a bias term added to a total weighted sum of inputs to serve as a threshold to shift the activation function. The propagation function computes the input to the succeeding node (successor) from the outputs of preceding nodes (predecessors) and may include the bias value.

Secondly, in case the iteration starts at step d), data of projections of the imaging procedure, in particular a medical (CT) scan preferably using the CT scanner, are received as input to the first trained neural network NNsin.

In case the iteration starts at step f), data of projections of the imaging procedure, in particular a medical (CT) scan preferably using the CT scanner, are received as input to the (weighted) filtered backward projection or rather the backward-projector.

In case the iteration starts at step g), data of a volume of the imaging procedure, in particular a medical (CT) scan preferably using the CT scanner, are received as input to the second trained neural network NNvol.

In case the iteration starts at step i), data of a volume of the imaging procedure, in particular a medical (CT) scan preferably using the CT scanner, are received as input to the forward-projection or rather the forward-projector.

Projections are any raw-data acquired during an imaging process, in particular a medical scan like CT, magnetic resonance imaging (MRI), ultra sound imaging, and the like. Preferably, the projections are sinograms acquired during a CT scan of a subject. Thereby, the subject is radiated with x-ray beams from one side and the remaining radiation is collected at the opposite side. The x-ray beam may be emitted as point (0D), line (1D), or preferably cone (2D) and the resulting projection may accordingly be one intensity (0D), an array of intensities (1D), or a matrix/an image of intensities (2D). The data of projections may be one or more intensity values of one or more of the projections. For example, the data of projections may be the intensity value of one central pixel x and the intensity values of a predefined amount of neighbours o of the central pixel x of one of the projections.

The tuning of filter parameters and filtering of the projections and volume are iteratively executed. As an example, one iteration staring a step d) is described in the following. However, as already mentioned, the first iteration and thus any subsequent iteration may start at either step f) or step g) or step i) instead of step d).

In the first iteration, the received data of projections of the imaging procedure is used as input to the first neural network NNsin. Alternatively, forward-projected projections form a volume of the imaging procedure (medical (CT) scan) may be used as input to the first trained neural network NNsin in the first iteration. In the subsequent iterations, forward-projected projections based on volumes of the respective previous iteration are used as input to the first trained neural network NNsin.

The data of projections, for example a central pixel x and a predefined number of surrounding pixels/neighbours o of one projection represented as an image of intensities, is input to the first trained neural network NNsin. Based on the input data of projections, the first trained neural network NNsin automatically tunes the spatial projection filter parameter σs,sin and additionally or alternatively the intensity projection filter parameter σi,sin. In particular, the first neural network may output a value of one or both projection filter parameters or a respective change action (e.g. increase/decrease by X % [percent]) for the value of one or both projection filter parameters.

After automatic tuning of the projection filter parameter(s), each of the projections is filtered with the projection (J)BF F sin based on the respective projection filter parameters σs,sin/σi,sin. Thereby, each projection may be filtered using the same or different projection filter parameters. The projection (J)BF may be implemented on a projection filter module. The projection filter module may be a software module or a hardware module (e.g. data processing system, dedicated processing unit, etc.).

The filtered projections are backward-projected into a volume via the (W)FBP. Preferably, the FDK algorithm is used to back-project the volume from the filtered projections. The FDK algorithm is a widely used FBP algorithm for 3D image/volume reconstruction from cone-beam (CB) projections measured with a circular orbit of the x-ray scanner. A property of said algorithm is that the integral of the reconstructed image along any axial line orthogonal to the plane of the orbit is exact when the cone-beam projections are not truncated. The (W)FBP may be implemented on a backward-projection module. The backward-projection module may be a software module or a hardware module (e.g. data processing system, dedicated processing unit, etc.).

Alternatively, the FBP or fan beam scans or WFBP for helical cone beam scans can be used.

The data of the backward-projected volume is input to the second neural network NNvol.

The data of the backward-projected volume, for example a central voxel and a predefined number of surrounding voxels/neighbours o of the volume, is input to the second trained neural network NNvol. Based on the input data of the back-projected volume the second trained neural network NNvol automatically tunes the spatial volume filter parameter σs,vol and additionally or alternatively the intensity volume filter parameter σi,vol. In particular, the second trained neural network may output a value of one or both volume filter parameters or a respective change action (e.g. increase/decrease by X % [percent]) for the value of one or both volume filter parameters.

After automatic tuning of the volume filter parameter(s), the volume is filtered with the volume (J)BF Fvol based on the respective volume filter parameters σs,vol/σi,vol. Thereby, each voxel may be filtered using the same or different volume filter parameters. The volume (J)BF may be implemented on a volume filter module. The volume filter module may be a software module or a hardware module (e.g. data processing system, dedicated processing unit, etc.).

The filtered volume is either forward projected into projections, which are input to the first neural network NNsin for automatically tuning the projection filter parameter(s) in the next iteration, or output as final filtered i.e. reconstructed medical volume or images. In case the filtered volume does not meet the predefined quality criterion (e.g. predefined limit value for the Gradient Structural Similarity Index (GSSIM) or the like of the filtered image or predefined number of iterations), a further iteration is initiated by forwarding the filtered volume to the forward-projection, which may be implemented on a forward-projection module, and inputting the forward-projected projections to the first neural network NNsin. The forward-projection module may be a software module or a hardware module (e.g. data processing system, dedicated processing unit, etc.). In case the filtered volume meets the predefined quality criterion (e.g. predefined limit value for the GSSIM or the like of the filtered image), the filtered volume is output to an external output device like a monitor for a user (e.g. radiologist) as the reconstructed medical volume/images.

The first neural network NNsin and the second neural network NNvol have to be trained for automatically tuning the respective filter parameters of the two (J)BFs.

A learning or training rule/paradigm is an algorithm which modifies the parameters of a respective NN in order for a given input to the NN to produce a favoured output. This training typically amounts to modifying the weights and/or thresholds of the variables within the NN. Given a specific task to solve and a class of functions, learning/training device or apparatus using a set of observations (training input data of the training data) to find the one function of the class of functions, which solves the task in some optimal sense (corresponding labels or ground truth data of the training data). This entails defining a cost function or rather a loss function such that for the optimal solution the cost/loss is minimal and no other solution has a cost/loss less than the cost/loss of the optimal solution. The cost function or rather loss function is an important concept in learning/training, as it is a measure of how far away a particular solution is from an optimal solution to the problem to be solved. Learning/training algorithms search through the solution space to find a function that has the smallest possible cost/loss. For applications where the solution is data dependent, the cost/loss must necessarily be a function of the observations, otherwise the model would not relate to the data. It is frequently defined as a statistic to which only approximations can be made. It is possible to define an arbitrary cost function or rather loss function, however, a particular cost/loss function may be used either because it has desirable properties (e.g. convexity) or because it arises naturally from a particular formulation of the problem.

A NN can be discriminatively trained with a standard backpropagation algorithm. Backpropagation is a method to calculate the gradient of a loss function (produces the cost associated with a given state) with respect to the weights in the NN. The weight updates of backpropagation can be done via stochastic gradient descent. The choice of the loss function depends on factors such as the learning type (e.g. supervised, unsupervised, reinforcement etc.) and the activation function. Commonly, the activation function and loss function are the softmax function and cross-entropy function, respectively.

In other words, training a NN essentially means selecting one model from the set of allowed models (or, in a Bayesian framework, determining a distribution over the set of allowed models) that minimizes the cost or loss. Commonly some form of gradient descent is deployed, using backpropagation to compute the actual gradients. This is done by simply taking the derivative of the cost/loss function with respect to the network parameters and then changing those parameters in a gradient-related direction.

Backpropagation training algorithms fall into three categories: steepest descent (with variable learning rate and momentum, resilient backpropagation), quasi-Newton (Broyden-Fletcher-Goldfarb-Shanno, one step secant), Levenberg-Marquardt and conjugate gradient (Fletcher-Reeves update, Polak-Ribiére update, Powell-Beale restart, scaled conjugate gradient).

Common training paradigms include supervised learning, unsupervised learning and reinforcement learning. Supervised learning uses a set of example pairs and the aim is to find a function in the allowed class of functions that matches the examples. In other words, the mapping implied by the data is inferred; the cost/loss function is related to the mismatch between the mapping of the NN and the data and it implicitly contains prior knowledge about the problem domain. The cost/loss may be the mean-squared error, which tries to minimize the average squared error between the NN's output and a target value over all the example pairs. Minimizing this cost/loss using gradient descent for the class of NNs called multilayer perceptrons (MLP), produces the backpropagation algorithm for training NNs. In unsupervised learning, some data is given and the cost/loss function to be minimized that can be any function of the data and the NN's output. The cost/loss function is dependent on the task and any a priori assumptions (e.g. implicit properties or parameters of the model, observed variables etc.). In reinforcement learning, data is usually not given, but generated by an agent's interactions with the environment. At each point in time the agent performs an action and the environment generates an observation and an instantaneous cost or loss according to some (usually unknown) dynamics. The aim is to discover a policy for selecting actions that minimizes some measure of a long-term cost/loss, e.g. the expected cumulative cost/loss. The environment's dynamics and the long-term cost/loss for each policy are usually unknown, but may also be estimated. The environment is commonly modelled as a Markov decision process (MDP) with states and actions with the following probability distributions: the instantaneous cost distribution, the observation distribution and the transition, while a policy is defined as the conditional distribution over actions given the observations. Taken together, the two then define a Markov chain (MC). The aim is to discover the policy (i.e., the MC) that minimizes the cost/loss.

The goal of training a NN is to optimize the weights and optionally other parameters of the NN such that the NN correctly maps input data provided at its input or rather input node(s) to output data at its output or rather output node(s). First, input data (one randomly selected sample of the training data set) is forward-propagated through the NN by providing the input data at the input of the NN. As a result of the forward-propagation a current output is computed by the NN based on the input data provided to the input node(s) and the internal weights of the NN. The current output is provided at the output node(s) of the NN. Then the current output is compared to the label or ground truth data of the training data set that is associated with the (randomly selected) input data. The comparison can be done by an error function or cost/loss function that computes an error/cost/loss. In order to archive training or learning the error/cost/loss is back-propagated by adapting the weights of the NN based on the computed error/cost/loss.

According to one or more example embodiments, both neural networks are trained back to back/jointly using a reinforcement learning algorithm.

Firstly, a training set is provided. The training set comprises training data of a predefined number of training volumes. For example, the AAMP Low Dose CT Grand Challenge dataset (C. H. Mccollough, "Low Dose CT Grand Challenge", 2016) may be used for training the first and second neural networks. The training data of training volumes comprises corresponding data of respective projections.

Secondly, the (untrained) first neural network NNsin and the second neural network NNvol are provided. The two neural networks may be implemented on a common or each on a separate (training) machine learning module. The (training) machine learning module(s) may be a software module or a hardware module (e.g. data processing system, dedicated processing unit, etc.).

The first neural network NNsin is configured to receive data of projections as input, for example at an input layer. The data of projections may each comprise one central pixel and the predefined number of neighbours o of the central pixel x of one projection. The projections used for training may be forward projected from the received training volumes or be comprised in the training set. The first neural network NNsin is further configured to provide the spatial projection filter parameter $\sigma_{s,sin}$ and additionally or alternatively the intensity projection filter parameter $\sigma_{i,sin}$ of the projection (J)BF F sin as output, for example at an output layer. Between the input layer and the output layer at least one layer comprising at least two nodes may be comprised.

Likewise, the second neural network NNvol is configured to receive data of a volume as input, for example at an input layer. The data of the volume may comprise at least a part or all voxels of the volume each represented as central voxel together with the predefined number of neighbours o. The second neural network NNvol is further configured to provide the spatial volume filter parameter σs,vol and additionally or alternatively the intensity volume filter parameter σi,vol of the volume (J)BF Fvol as output, for example at an output layer. Between the input layer and the output layer at least one layer comprising at least two nodes may be comprised.

Afterwards, the first and second neural network are trained, in particular back to back/jointly, each based on a respective reward. Thereto a reinforcement learning algorithm may be used. The reward may, for example, be derived from comparing the quality of a projection or rather volume filtered with the current filter parameters with the quality of a precedingly filtered projection/volume. The weights of both neural networks are iteratively adjusted based on the respective reward until a predefined break criterion, for example a predefined number of iterations or a minimal difference between the weights of the current iteration and the weights of the preceding iteration, and the like, is met. The reward may be calculated based on comparing the current filtered projections with previous filtered projections or with ground truth (i.e.) projections comprised by the training set and, accordingly, based on comparing the current filtered volume with a previous filtered volume or a ground truth (i.e. ideal) volume comprised by the training set.

In particular, a Q-learning approach, a policy gradient or A3C approach may be used for training the first and second neural network.

The trained first and second neural network, according to one or more example embodiments, replace a human operator for tuning the filter parameters of the two (J)BFs in the projection/projection domain and the volume/image domain, respectively.

With the reconstruction, according to one or more example embodiments, using the trained first and second neural networks to automatically tune the filter parameters of the two (J)BFs for filtering the projections/projections as well as the volume, artefacts in the medical volume or rather medical images can be significantly reduced and the image quality, thus, further improved. At the same time, the time for tuning the filter parameters is reduced and interpretability of the whole process nevertheless given, i.e. the iterative automatic tuning of the filter parameters via the first and second neural network is retraceable (no black-box).

According to a refinement of one or more example embodiments, the spatial projection filter parameter σs,sin and the intensity projection filter parameter σi,sin are tuned for each of the projections, in the step d).

Likewise, in training the first neural network NNsin more than one projection forward projected from the same training volume are used to train the first neural network NNsin for automatically tuning the spatial projection filter parameter σs,sin and additionally or alternatively the intensity projection filter parameter σi,sin.

Instead of using one pair of projection filter parameters for filtering all projections, a respective pair (or one of the respective pair) of projection filter parameters is automatically tuned for filtering each of the received projections. Since noise in the projection domain follows a Poisson distribution, global filter parameters for each projection are sufficient to remove the noise. Therefore, only an optimal set of filter parameters for each of the received projections needs to be automatically tuned, instead of for each pixel of each received projection.

Thus, the computation time is significantly reduced, while the quality of the reconstructed medical volume/images is not significantly reduced.

According to a refinement of one or more example embodiments, the spatial volume filter parameter σs,vol and additionally or alternatively the intensity volume filter parameter σi,vol are tuned for each voxel of the volume, in step h).

Likewise, in training the second neural network NNsin more than one voxel of the volume used for training is used to train the second neural network NNvol for automatically tuning the spatial volume filter parameter σs,vol and additionally or alternatively the intensity volume filter parameter σi,vol.

The noise in the volume/image domain is non-linear and, consequently, the two volume filter parameters are automatically tuned for each voxel of the volume instead of using only one global set of volume filter parameters for the whole volume.

Thus, the quality of the reconstructed medical volume/images is further increased.

According to a refinement of one or more example embodiments, the first neural network NNsin and additionally or alternatively the second neural network NNvol are convolutional neural networks (CNN).

CNN is a class of deep neural networks, most commonly applied in analysing images. In CNNs weights are shared in the architecture and they have translation invariance characteristics. CNNs are regularized versions of multilayer perceptrons (fully connected networks). Each neuron in one layer is connected to all neurons in the next layer. For regularization (to avoid over-fitting) CNNs take advantage of the hierarchical pattern in data and assemble more complex patterns using smaller and simpler patterns. Therefore, on the scale of connectedness and complexity, CNNs are on the lower extreme. CNNs use relatively little pre-processing compared to other classification algorithms. This means that the network learns the filters that in traditional algorithms were hand-engineered. This independence from prior knowledge and human effort in feature design is a major advantage.

The first neural network NNsin for filtering the projections may in particular be a 2D CNN. The input of 2D CNNs is a matrix (2 directions, e.g. (x,y)) of a given size (e.g. W×H) to calculate using a filter of a given size (e.g. k×k) the convolution output-shape as matrix of the same or a different given size (e.g. W×H) (e.g. Sobel Egde FIlter).

The second neural network NNvol may in particular be a 3D CNN. The input of 3D CNNs is a volume/3D tensor (3 directions, e.g. (x,y,z)) of a given size (e.g. W×H×L) to calculate using a filter of a given size (e.g. k×k×d, where d<L) the convolution output-shape as volume/tensor of the same or a different given size (e.g. W×H×L) (e.g. C3D).

The first neural network NNsin is a first (2D) convolutional neural network CNNsin. Additionally or alternatively, the second neural network NNvol is a second (3D) convolutional neural network CNNvol. Both convolutional neural networks may each comprise an input layer, several filter layers, a condensation layer, and an output layer. The input layer of the first neural network NNsin may be configured to receive a central pixel x with neighbours o of a projection, for example the input layer may be configured to receive 5×5 pixels (1 central pixel x and 24 neighbours o) of a projection. The input layer of the second neural network NNvol may be configured to receive a central voxel x with neighbours o of a volume, for example the input layer may be configured to receive 5×5×5 voxel (1 central voxel x and 124 neighbours o) of a volume.

The first and additionally or alternatively the second neural network may comprise a bifurcation into two branches. For example the first or second neural network may comprise:
- a first layer of 32 (2D/3D) filters subsequent to the input layer, wherein each filter reduces the size of the input;
- a second layer of 64 (2D/3D) filters subsequent to the first layer, wherein each filter reduces the size of the input;
- a parameter branch subsequent to the second layer comprising:
- a first parameter layer of 64 (2D/3D) filters, wherein each filter reduces the size of the input;
- a parameter condensation layer of 128 nodes;
- a parameter output layer of two nodes, one node for each of the two filter parameters;
- an action branch subsequent to the second layer comprising:
- a first action layer of 128 (2D/3D) filters, wherein each filter reduces the size of the input;
- a second action layer of 128 (2D/3D) filters;
- an action condensation layer of 256 nodes; and
- an action output layer of five nodes, one node for each possible change action to the filter parameter.

The number of filters in each layer according to an advantageous example may be adapted depending, e.g., on the datasate or the like. The utilization of convolutional neural network(s) enables particular precise and fast automatic tuning of the filter parameters.

According to a refinement of one or more example embodiments, at least one of the group comprising the first neural network NNsin and the second neural network NNvol is configured to automatically select one of the respective spatial filter parameter σs,sin/σs,vol and intensity filter parameter σi,sin/σi,vol, respectively, to be tuned.

The first neural network NNsin and additionally or alternatively the second neural network NNvol selects one of the respective two filter parameters to be automatically tuned. Consequently, in each iteration only one of the two filter parameters for one or both of the projection (J)BF and the volume (J)BF is automatically tuned.

For example, via the parameter branch of the respective neural network the one parameter of the spatial projection/volume filter parameter and the intensity projection/volume filter parameter, whose change will contribute most to denoising the received projection/volume, is chosen for automatic tuning.

Thereby, the amount of iterations and, thus, time needed to automatically tune the filter parameters is further reduced.

According to a refinement of one or more example embodiments, at least one of the group comprising the first neural network NNsin and the second neural network NNvol is configured to output one of a predefined number of actions to tune the respective filter parameter(s) σs,sin/σs,vol/σi,sin/σi,vol.

The first neural network NNsin and additionally or alternatively the second neural network NNvol selects one action of the predefined number of actions to tune the (selected) filter parameter(s). Consequently, in each iteration the one selected filter parameter or both filter parameters of the projection (J)BF and additionally or alternatively the volume (J)BF is automatically tuned by applying one specific action of tuning (e.g. increase parameter value by 10% [percent]).

For example, via the action branch of the respective neural network the one action of the predefined number of actions to change the (selected) filter parameter(s), whose change will contribute most to denoising the received projection/volume, is chosen for automatic tuning.

Thereby, the amount of iterations and, thus, time needed to automatically tune the filter parameters is further reduced.

According to a further refinement of one or more example embodiments, the predefined number of actions to tune the respective filter parameter(s) σs,sin/σs,vol/σi,sin/σi,vol comprise "increase parameter value by 50%"; "increase parameter value by 10%"; "do not change parameter value"; "decrease parameter value by 10%"; and "decrease parameter value by 50%".

With these five predefined actions to change the respective (selected) filter parameter(s), the amount of iterations and, thus, time needed to automatically tune the filter parameters is even further reduced.

According to a refinement of one or more example embodiments, the step t4) of training the first neural network NNsin and the second neural network NNvol comprises the following sub-steps:

t4.1) Randomly selecting one or more of the training volumes and either selecting training projections comprised in the corresponding training data or forward-projecting projections from the selected training volume as current projections; and for each selected training volume:

t4.2) Filtering the current projections with the projection (J)BF F sin based on the projection filter parameters σs,sin, σi,sin tuned by the first neural network NNsin based on current weights of the first neural network Nnsin;

t4.3) Updating weights of the first neural network NNsin based on the reward estimated from a volume backward-projected from the filtered projections and a volume backward-projected based on the current projections and, in case a predefined first stop criterion is not met, forwarding the filtered projections as current projections and returning to SUB-step t4.2);

t4.4) Forwarding the volume backward-projected from the filtered projections as current volume;

t4.5) Filtering the current volume with the volume (J)BF Fvol based on the volume filter parameters σs,vol, σi,vol tuned by the second neural network NNvol based on current weights of the second neural network Nnvol;

t4.6) Updating weights of the second neural network NNvol based on the reward estimated from the filtered volume and the current volume and, in case a predefined second stop criterion is not met, forwarding the filtered volume as current volume and returning to sub-step t4.5).

The first neural network NNsin for projection filter parameter tuning may be trained with the similarity of the simulated projections to the collected data as a reward function. The second neural network NNvol for volume filter parameter tuning network may be trained using a reward network which calculates the noise content of the image as well as simulating an anthropomorphic model observer.

One or more training volumes or rather the corresponding training data are randomly selected from the training set. For each of the one or more selected training volumes the training steps t4.1) to 4.6) are executed in order to train the first neural network NNsin and the second neural network NNvol.

In case the training data comprised in the training set includes the corresponding training projections for each of the training volumes, the training projections pertaining to the respective randomly selected one or more training volumes are forwarded as the current projections for the first iteration. In case the training data comprised in the training set does not include training projections, projections are forward-projected from the selected one or more training volume(s) as the current projections for the first iteration.

The sub-steps t4.2) and t4.3) are iteratively executed for tuning the first neural network NNsin until the first stop criterion is met (e.g. predefined number of iterations, value of a quality measure, difference between current filtered and previous projection/volume).

The current projections are filtered with the projection (J)BF F sin using the current projection filter parameters σs,sin, σi,sin. In the first iteration, the projection filter parameters σs,sin, σi,sin are set to a predefined value or have a value tuned for a previously selected training volume. In each subsequent iteration, the projection filter parameters σs,sin, σi,sin have a value tuned by the first neural network NNsin in the preceding iteration. Thereby, the tuning of the projection filter parameters σs,sin, σi,sin in the previous iteration is based on the current (updated in the preceding iteration) weights of the first neural network NNsin.

For updating the weights of the first neural network NNsin the corresponding reward is estimated. The reward is estimated or calculated by comparing the volume backward-projected (e.g. (W)FBP) from the filtered projections with the volume backward-projected (e.g. (W)FBP) from the current projections. Based on the estimated reward, the weights of the first neural Network NNsin are adjusted. In case the first stop criterion is not met, the filtered projections are forwarded as the current projections and a new iteration at sub-step t4.2) is started.

In case the first stop criterion is met, the volume backward-projected from the filtered projections is forwarded as the current volume and the training is continued at sub-step t4.5).

The sub-steps t4.5) and t4.6) are iteratively executed for tuning the second neural network NNvol until the second stop criterion is met (e.g. predefined number of iterations, value of a quality measure, difference between current filtered and previous projection/volume).

The current volume is filtered with the volume (J)BF Fvol using the current volume filter parameters σs,vol, σi,vol. In the first iteration, the volume filter parameters σs,vol, σi,vol are set to a predefined value or have a value tuned for a previously selected training volume. In each subsequent iteration, the volume filter parameters σs,vol, σi,vol have a value tuned by the second neural network NNvol in the preceding iteration. Thereby, the tuning of the volume filter parameters σs,vol, σi,vol in the previous iteration is based on the current (updated in the preceding iteration) weights of the second neural network NNvol.

For updating the weights of the second neural network NNvol the corresponding reward is estimated. The reward is estimated or calculated by comparing the filtered volume with the current volume. Based on the estimated reward, the weights of the second neural Network NNvol are adjusted. In case the second stop criterion is not met, the filtered volume is forwarded as the current volume and a new iteration at sub-step t4.5) is started.

In case the second stop criterion is met, the training of the first and second neural network based on the current selected training volume is stopped. In case, there have been randomly selected more than one training volumes for training the two neural networks, the training is continued at sub-step 4.2) with the training data of the next randomly selected training volume.

Preferably, the first and second stop criterion may each be a predefined number of iterations.

With the reward-based training of the first and second neural network, the time for training both neural networks is significantly reduced.

According to a refinement of one or more example embodiments, the first neural network NNsin is trained by a Q-learning approach based on the reward estimated using a reward network Nrew. The weights of the first neural network NNsin are updated based on the reward estimated from the backward-projected filtered projections and backward-projected current projections using the reward network Nrew. Additionally or alternatively, The second neural network NNvol is trained by a Q-learning approach based on the reward estimated using the reward network Nrew. The weights of the second neural network NNvol are updated based on the reward estimated from the filtered volume and current volume using the reward network Nrew.

Q-learning approaches or algorithms are reinforcement learning approaches/algorithms to learn quality of actions telling an agent what action to take under what circumstances. For any finite Markov decision process (FMDP, mathematical framework for modelling decision making in situations where outcomes are partly random and partly under the control of a decision maker) Q-learning approaches/algorithms find an optimal policy in the sense of maximizing the expected value of the total reward over any and all successive steps, starting from the current state. Q-learning algorithms can identify an optimal action-selection policy for any given FMDP, given infinite exploration time and a partly-random policy. "Q" names the function that the algorithm computes with the maximum expected rewards for an action taken in a given state.

To achieve improved image quality based on the automatically tuned filter parameters, a policy has to be learned, which tunes the filter parameters such as to create an optimal image. This policy is learned via the Q-learning approach, defined by the following equation:

$$Q^*(s, a) = \max_\pi [r^k + \gamma r^{k+1} + \gamma^2 r^{k+2} + \ldots \mid s_k = s, a_k = a, \pi],$$

where Q* is the optimal action value to be achieved, π is the action choosing policy, s is the current state, and a is the action chosen at state s. a is defined as a function of parameter p and tuning strength t.

A property of Q*(s,a) (as described in Bellman, "Dynamic Programming," Science, vol. 153, no. 3731, pp. 34-37, 1966) is the following:

$$Q^*(s, a) = r + \gamma \cdot \max_{a'} Q^*(s', a'),$$

where r is the reward achieved by the optimal action a at s. s' is the state observed when a is taken at s. The value action function is parametrised with weights W, which can be determined by penalizing the deviation from the Bellman equation above. This deviation is represented by the following equation for the loss L:

$$L(W) = \left[r + \gamma \cdot \max_{a'} Q(s', a'; W) - Q(s, a; W)\right]^2$$

Then, a new variable W' is introduced, which represents an older version of the weights. Further, double deep-Q-learning may be introduced to prevent overestimations the neural networks. The loss L is then defined as:

$$L(W) = \left[r + \gamma Q\left(s', Q\max_{a'} Q(s', a'; W); W'\right) - Q(s, a; W)\right]^2$$

As described further above, the first neural network NNsin and additionally or alternatively the second neural network NNvol may have two paths, one path to choose the filter parameter to be tuned, and another path to select an action to tune it. Therefore, the above loss function is split into two parts to train the two neural networks given as:

$$L(W) = \left[2r + \gamma Q\left(s', Q\max_{p'} Q(s', p'; W); W'\right) + \gamma Q\left(s', Q\max_{t'} Q(s', t'; W); W'\right) - (Q(s, p; W) + Q(s, t; W))\right]^2,$$

where p, p' and t, t' represent the path for parameter selection and action selection, respectively.

With the Q-learning approach both neural networks are trained even more efficiently.

According to a further refinement of one or more example embodiments, the reward network Nrew is a neural network trained to predict a quality score IRQM for estimating the reward.

A neural network, in particular a convolutional neural network, is utilized to predict the quality score IRQM, which is based on the GSSIM, from current (noisy) volumes/images without having to compare the latter to a reference (e.g noise-free volume/image). The reward (convolutional) neural network may include four convolutional layers with 3×3 kernels, followed by a global average pooling layer and a fully connected layer. The convolutional layers may contain 16, 16, 32, and 32 filters. The fully connected layer may contain 32 neurons. Each layer may be followed by an eLU activation layer.

The target for training the reward network to predict the quality score IRQM from current (noisy) volumes or images can, for example, be represented by the following equation:

$$T(IM_1) = GSSIM(IM_1, IM_2) + \frac{1}{\frac{\text{mean}\left((IM_1 - IM_2)^2\right)}{ROI} + 1}$$

where IM1 is the current (noisy) volume/image, IM2 is the clean (noise-free) volume/image, and GSSIM is the gradient structural similarity metric. The second term attempts to measure the noise power in the volume. ROI is the receptive field of the network (e.g. 9×9). The reward network Nrew may have been trained on a subset of five patients reconstructed at standard, 50%, and 25% dose. The dataset may be augmented by flips, rotations, and Gaussian blurs. Random patches of size 32, 48, 64, and 96 may have been extracted for training the reward network Nrew. Optimization may have been performed using the Adam optimizer (D. P. Kingma and J. L. Bai, "Adam: A Method for Stochastic Optimization," in International Conference on Learning Representations, 2015) with a learning rate of 1×10-4 over 30 epochs.

Using the above described (convolutional) neural network as the reward network Nrew is particularly efficient for training.

Figure 4:
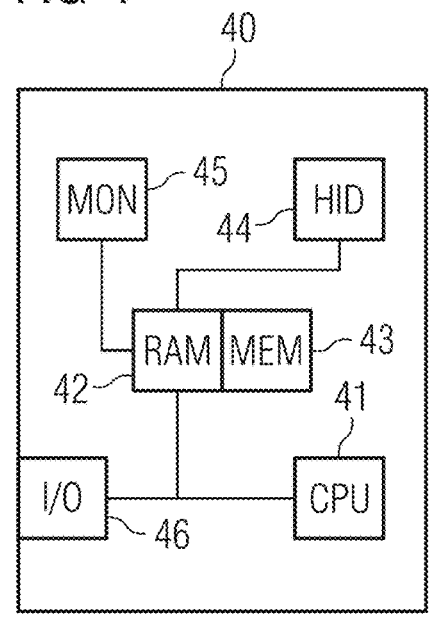
FIG. 4 is a schematic view of the data processing system, according to example embodiments, for iteratively reconstructing medical images or a medical volume using deep learning.

In FIG. 1 an example embodiment of the computer-implemented method of iteratively reconstructing medical images or a medical volume, in particular CT images or a CT volume, using deep learning according to the first aspect of example embodiments and of the computer program according to the second aspect of example embodiments are schematically depicted. The computer program comprises instructions which, when executed on a data processing system (e.g. the data processing system as schematically depicted in FIG. 4), cause the system to execute the steps of the method of iteratively reconstructing medical (CT) images or a medical (CT) volume using deep learning.

The method may comprise the optional initial or preparatory steps a) of providing 1 a first trained neural network NNsin; b) of providing 2 a second trained neural network NNvol; and c) of receiving 3 data of projections of an imaging procedure, in particular a medical (CT) scan, and/or data of volumes of the imaging procedure, in particular a medical (CT) scan. The method further comprises the iterative steps d) of automatically tuning 4 projection filter parameters; e) of filtering 5 the projections; f) of backward-projecting 6 a volume; g) of automatically tuning 7 volume filter parameters; h) of filtering 8 the volume; and i) of forward-projecting 9 projections; as well as the final step j) of outputting 10 the filtered volume.

In step a) of providing the first trained neural network NNsin, the first trained neural network NNsin, which is configured to receive data of projections as input and to provide a spatial projection filter parameter σs,sin and additionally or alternatively an intensity projection filter parameter σi,sin of a projection (J)BF F sin as output, is provided. The first trained neural network NNsin may be implemented on a first machine learning (software or hardware) module (21 in FIG. 2).

In step b) of providing the second trained neural network NNvol, the second trained neural network NNvol, which is configured to receive data of a volume as input and to provide a spatial volume filter parameter σs,vol and additionally or alternatively an intensity volume filter parameter σi,vol of a volume (J)BF Fvol as output, is provided. The second trained neural network NNvol may be implemented on a second machine learning (software or hardware) module (24 in FIG. 2).

In step c) data of projections and additionally or alternatively data of a volume of the imaging procedure (medical (CT) scan) is received. In case data of projections of the medical (CT) scan is received, the iterations of steps d) to i) may start at step d) of automatically tuning (4) the projection filter parameters or step f) of backward-projecting a volume. In case data of a volume of the imaging procedure (medical (CT) scan) is received, the iterations of steps d) to i) may start at step g) of automatically tuning (7) the volume filter parameters or step i) of forward-projecting projections.

In the following the method is exemplarily described staring at step d) in the first iteration.

In step d) the spatial projection filter parameter σs,sin and additionally or alternatively the intensity projection filter parameter σi,sin of a of the projection (J)BF F sin is automatically tuned by the first trained neural network NNsin. The automatic tuning is based on the data of projections of the imaging procedure (medical (CT) scan) in the first iteration. In the subsequent iterations, the automatic tuning is based on data of forward projected projections (in step i)) of preceding iterations. The spatial projection filter parameter σs,sin and the intensity projection filter parameter σi,sin may be set to a predefined staring value between 1 and 5 in the first iteration.

In particular, the first neural network NNsin may by be configured and trained to automatically tune one or both of the projection filter parameters σs,sin/σi,sin for each of the projections. For example, if 16 projections are received, the projection filter parameter(s) are exclusively tuned for each of the 16 projections.

Preferably, the first neural network NNsin may be configured and trained to select and automatically tune either the spatial projection filter parameter σs,sin or the intensity projection filter parameter σi,sin. Further, the first neural network NNsin may, preferably, be configured and trained to output one of a predefined number of actions to tune the respective projection filter parameter(s) σs,sin/σi,sin, in particular, one of the actions: "increase parameter value by 50%"; "increase parameter value by 10%"; "do not change parameter value"; "decrease parameter value by 10%"; and "decrease parameter value by 50%".

In step e) the projections or rather each pixel of the projections are filtered with the projection (J)BF F sin based on the automatically tuned projection filter parameters (each projection with its own exclusive set of projection filter parameters). The projection (J)BF F sin may be implemented on a first filter (software or hardware) module (22 in FIG. 2). In particular, the projection (J)BF F sin may be defined by the following equation:

$$FT_{sin}(x) = \frac{\sum_{o \in N(x)} IN_{sin}(o) G_{\sigma_s,sin}(x-o) G_{\sigma_i,sin}(I_{(g)}(x) - I_{(g)}(o))}{\sum_{o \in N(x)} G_{\sigma_s,sin}(x-o) G_{\sigma_i,sin}(I_{(g)}(x) - I_{(g)}(o))}, \text{ with}$$

$$G_{\sigma_i,sin}(I_{(g)}(x) - I_{(g)}(o)) = \frac{1}{\sqrt{2\pi}\,\sigma_{i,sin}} e^{-\left(\frac{(\delta(I_{(g)}(x),I_{(g)}(o)))^2}{2\sigma_{i,sin}^2}\right)} \text{ and}$$

$$G_{\sigma_s,sin}(x-o) = \frac{1}{\sqrt{2\pi}\,\sigma_{s,sin}} e^{-\left(\frac{(d(x,o))^2}{2\sigma_{s,sin}^2}\right)},$$

where FTsin is the filtered projection, INsin is the unfiltered projection, I is the intensity (for the BF), Ig is the intensity in the guide image/projection (for the JBF), x is a central pixel of the projection, o is one of the neighbours N of the central pixel (e.g. 24 neighbours). Each pixel x of a projection to be filtered is once selected as the central pixel and filtered according to above given equation with the exclusive projection filter parameters of the projection.

In step f) the filtered projections are used to backward-project a volume therefrom using a (W)FBP, in particular the FDK algorithm. The (W)FBP may be implemented on a backward-projector (software or hardware) module (23 in FIG. 2).

In step g) the spatial volume filter parameter σs,vol and additionally or alternatively the intensity volume filter parameter σi,vol of a of the volume (J)BF Fvol is automatically tuned by the second trained neural network NNvol. The automatic tuning is based on the data of the backward-projected volume (in step f)). The spatial volume filter parameter σs,vol and the intensity volume filter parameter σi,vol may be set to a predefined staring value between 1 and 25 in the first iteration.

In particular, the second neural network NNvol may by be configured and trained to automatically tune one or both of the volume filter parameters σs,vol/σi,vol for each of the voxels of the volume. For example, if 64×64×16 voxels of the volume are received, the volume filter parameter(s) are exclusively tuned for each of the 65.536 voxels.

Preferably, the second neural network NNvol may be configured and trained to select and automatically tune either the spatial volume filter parameter σs,vol or the intensity volume filter parameter σi,vol. Further, the second neural network NNvol may, preferably, be configured and trained to output one of a predefined number of actions to tune the respective volume filter parameter(s) σs,vol/σi,vol, in particular, one of the actions: "increase parameter value by 50%"; "increase parameter value by 10%"; "do not change parameter value"; "decrease parameter value by 10%"; and "decrease parameter value by 50%".

In step h) the volume or rather each voxel x of the volume is filtered with the volume (J)BF Fvol based on the automatically tuned volume filter parameters (each voxel with its own exclusive set of volume filter parameters). The volume (J)BF Fvol may be implemented on a second filter (software or hardware) module (25 in FIG. 2). In particular, the volume (J)BF Fvol may be defined by the following equation:

$$FT_{vol}(x) = \frac{\sum_{o \in N(x)} IN_{vol}(o) G_{\sigma_s,vol}(x-o) G_{\sigma_i,vol}(I_{(g)}(x) - I_{(g)}(o))}{\sum_{o \in N(x)} G_{\sigma_s,vol}(x-o) G_{\sigma_i,vol}(I_{(g)}(x) - I_{(g)}(o))}, \text{ with}$$

$$G_{\sigma_i,vol}(I_{(g)}(x) - I_{(g)}(o)) = \frac{1}{\sqrt{2\pi}\,\sigma_{i,vol}} e^{-\left(\frac{(\delta(I_{(g)}(x),I_{(g)}(o)))^2}{2\sigma_{i,vol}^2}\right)} \text{ and}$$

$$G_{\sigma_s,vol}(x-o) = \frac{1}{\sqrt{2\pi}\,\sigma_{s,vol}} e^{-\left(\frac{(d(x,o))^2}{2\sigma_{s,vol}^2}\right)},$$

where FTvol is the filtered volume, INvol is the unfiltered volume, I is the intensity (for the BF), Ig is the intensity in the guide image/volume (for the JBF), x is a central voxel of the volume, o is one of the neighbours N of the central voxel (e.g. 124 neighbours). Each voxel x of a volume to be filtered is once selected as the central voxel and filtered according to above given equation with its own exclusive volume filter parameters.

In case the quality criterion QC is not met, the next iteration is initiated by continuing to step i). The quality criterion may be a limit value of the GSSIM of the filtered volume or a predefined number of iterations.

In step i) the filtered volume is used to forward-project projections therefrom using a forward-projection FP. In particular, a Radon transform (adapted to beam shape) can be applied directly. The forward-projection FP may be implemented on a forward-projector (software or hardware) module (26 in FIG. 2).

In case the quality criterion QC is met, the iterations are stopped and the method is continued at step j)

In step j) the filtered volume is output as the reconstructed (final) medical images or volume. The reconstructed (final) medical images or volume may be provided to an output device like a monitor to display the latter to a user (e.g. radiologist, etc.).

Figure 2:
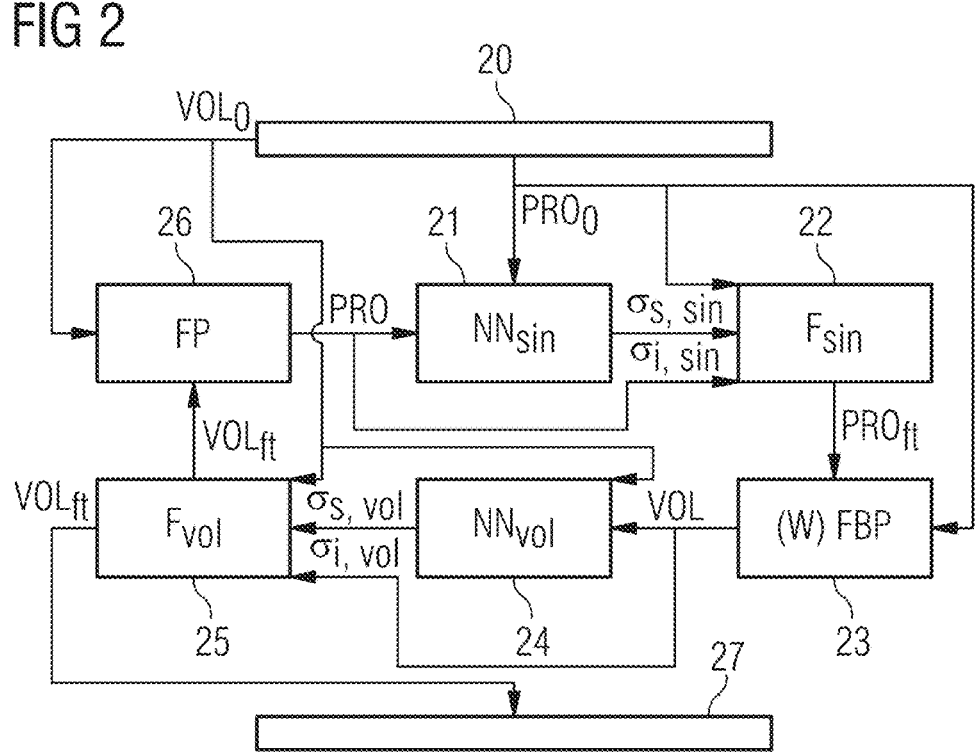
FIG. 2 is a schematic view of the first and second neural network NNsin, NNvol; the projection and volume (J)BF F sin, Fvol; the (W)FBP; and the forward-projection.

In FIG. 2 an example embodiment of the first and second neural network NNsin, NNvol; the projection and volume (J)BF F sin, Fvol; the (W)FBP; and the forward-projection; used in the method of FIG. 1 is schematically depicted.

Figure 5:
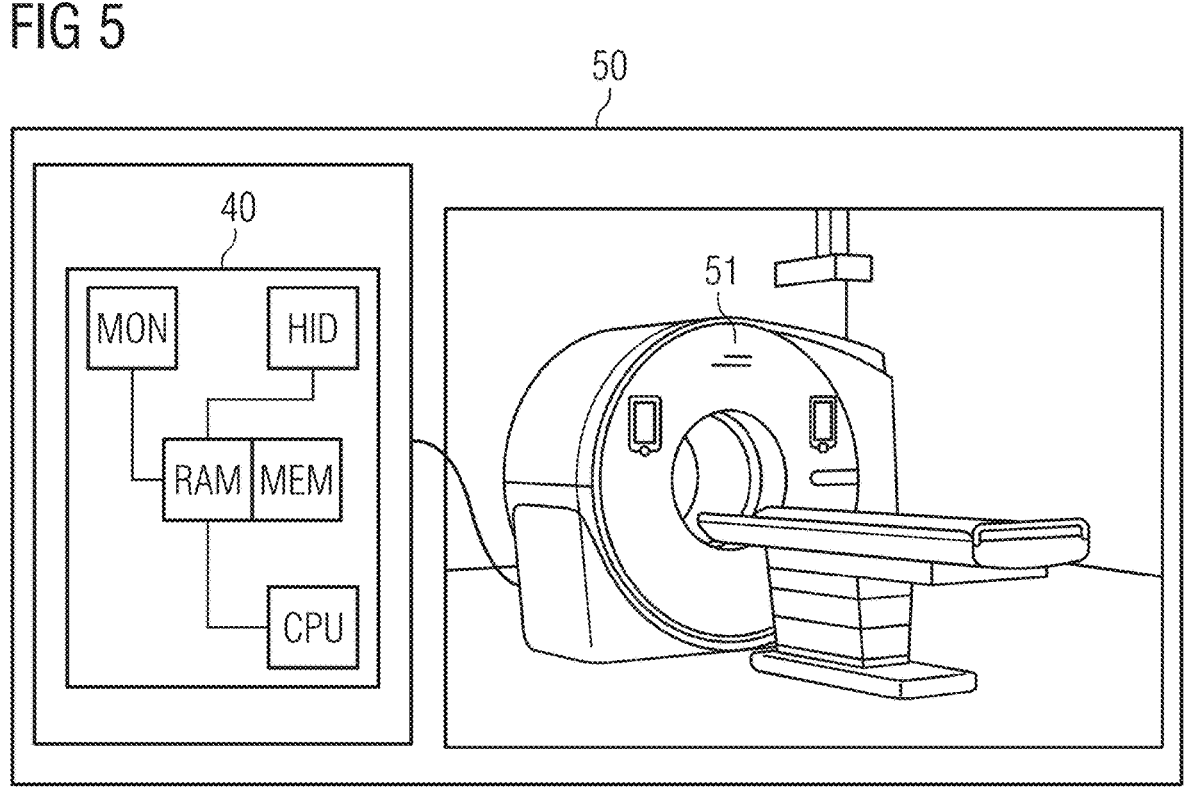
FIG. 5 is a schematic view of the CT system.

An input module or interface 20 is configured to receive data of projections PRO0 or data of a volume VOL0 of an imaging procedure (e.g. of a medical (CT) scan), which may have been conducted by a CT scanner (51 in FIG. 5).

The first neural network NNsin is implemented on a first machine learning module 21, which may be a software module (e.g. a class) or a hardware module (e.g. a processing unit).

The projection (J)BF F sin is implemented on a first filter module 22, which may be a software module (e.g. a class) or a hardware module (e.g. a processing unit). The first filter module 22 is communicatively connected to the first machine learning module 21 for receiving the automatically tuned projection filter parameter(s) σs,sin/oi, sin.

The (W)FBP is implemented on a backward-projector module 23, which may be a software module (e.g. a class) or a hardware module (e.g. a processing unit). The backward-projector module 23 is communicatively connected to the first filter module for receiving the filtered projections PROft.

The second neural network NNvol is implemented on a second machine learning module 24, which may be a software module (e.g. a class) or a hardware module (e.g. a processing unit). The second machine learning module 24 is communicatively connected to the backward-projector module 23 for receiving the back-ward projected volume VOL.

The volume (J)BF Fvol is implemented on a second filter module 25, which may be a software module (e.g. a class) or a hardware module (e.g. a processing unit). The second filter module 25 is communicatively connected to the second machine learning module 24 for receiving the automatically tuned volume filter parameter(s) σs,vol/oi,vol. The second filter module 25 is further communicatively connected to the backward-projector module 23 for receiving the backward-projected volume.

The FP is implemented on a forward-projector module 26, which may be a software module (e.g. a class) or a hardware module (e.g. a processing unit). The forward-projector module 26 is communicatively connected to the second filter module for receiving the filtered volume VOLft. The forward-projector module 26 is further communicatively connected to the first machine learning module 21 and to the first filter module 22 for forwarding the forward-projected projections PRO.

Depending on at which step of the method of FIG. 1 the first iteration starts, the input module 20 is communicatively connected to the first machine learning module 21 (start at step d)), to the first machine learning module 21 and the first filter module 22 (start at step d)), to the backward-projector module 23 (start at step f)), to the second machine learning module 24 and the second filter module 25 (start at step g)) or to the forward-projector module 26 (start at step i)).

A output module or interface 27 is communicatively connected to the second filter module 25 for receiving the filtered volume VOLft and configured to forward the filtered volume VOLft as the reconstructed (final) medical volume or images to an external module or device like a monitor (45 in FIG. 4).

Like above, the example case of starting the first iteration at step d) is described in the following. The input module 20 forwards the received data of projections PRO0 to the first machine learning module 21 such that the projection filter parameter (s) can be automatically tuned by the first neural network NNsin. Further, the input module 20 forwards the received data of projections PRO0 to the first filter module 22 such that the received projections of the imaging procedure (medical (CT) scan) can be filtered by the projection (J)BF based on the automatically tuned projection filter parameter(s).

The first neural network NNsin on the first machine learning module 21 automatically tunes the projection filter parameter(s) σs,sin/σi,sin based on the received projections PRO0 of the imaging procedure (medical (CT) scan) in the first iteration and based on the received forward-projected projections PRO in the subsequent iterations.

The projection (J)BF F sin on the first filter module 22 filters each of the received projections PRO0 of the imaging procedure (medical (CT) scan) in the first iteration and each of the received forward-projected projections PRO in the subsequent iterations into the filtered projections PROft.

The (W)FBP on the backward-projector module 23 backward-projects a volume VOL from the received filtered projections PROft.

The second neural network NNvol on the second machine learning module 24 automatically tunes the volume filter parameter(s) σs,vol/σi,vol based on the received backward-projected volume VOL.

The volume (J)BF Fvol on the second filter module 25 filters the received backward-projected volume VOL or rather each voxel of the received backward-projected volume VOL into the filtered (voxels of the) volume VOLft.

In case the quality criterion QC is not met, the FP on the forward-projector module 26 forward-projects projections PRO from the filtered volume VOLft and a further iteration starts at step d).

In case the quality criterion is met, the output module 27 provides the filtered volume VOLft as the reconstructed (final) medical volume or images to an external module or device (e.g. monitor).

Figure 3:
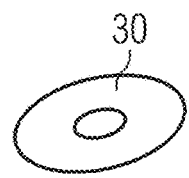
FIG. 3 is a schematic view of the computer-readable medium having stored thereon the computer program according to the second aspect of example embodiments.

In FIG. 3 an example embodiment of the computer-readable medium 30 according to the third aspect is schematically depicted.

Here, exemplarily a computer-readable storage disc 30 like a Compact Disc (CD), Digital Video Disc (DVD), High Definition DVD (HD DVD) or Blu-ray Disc (BD) has stored thereon the computer program according to the second aspect of example embodiments and as schematically depicted in FIG. 1. However, the computer-readable medium may also be a data storage like a magnetic storage/memory (e.g. magnetic-core memory, magnetic tape, magnetic card, magnet strip, magnet bubble storage, drum storage, hard disc drive, floppy disc or removable storage), an optical storage/memory (e.g. holographic memory, optical tape, Tesa tape, Laserdisc, Phasewriter (Phasewriter Dual, PD) or Ultra Density Optical (UDO)), a magneto-optical storage/memory (e.g. MiniDisc or Magneto-Optical Disk (MO-Disk)), a volatile semiconductor/solid state memory (e.g. Random Access Memory (RAM), Dynamic RAM (DRAM) or Static RAM (SRAM)) or a non-volatile semiconductor/solid state memory (e.g. Read Only Memory (ROM), Programmable ROM (PROM), Erasable PROM (EPROM), Electrically EPROM (EEPROM), Flash-EEPROM (e.g. USB-Stick), Ferroelectric RAM (FRAM), Magnetoresistive RAM (MRAM) or Phase-change RAM).

In FIG. 4 an example embodiment of the data processing system 40 according to the fourth aspect of example embodiments is schematically depicted.

The data processing system 40 may be a personal computer (PC), a laptop, a tablet, a server, a distributed system (e.g. cloud system) and the like. The data processing system 40 comprises a central processing unit (CPU) 41, a memory having a random-access memory (RAM) 42 and a non-volatile memory (MEM, e.g. hard disk) 43, a human interface device (HID, e.g. keyboard, mouse, touchscreen etc.) 44, an output device (MON, e.g. monitor, printer, speaker, etc.) 45 and an interface (I/O) 46 for receiving and sending data. The CPU 41, RAM 42, HID 44 MON 45 and I/O 46 are communicatively connected via a data bus. The RAM 42 and MEM 43 are communicatively connected via another data bus.

The computer program according to the second aspect of example embodiments and schematically depicted in FIG. 1 can be loaded into the RAM 42 from the MEM 43 or another computer-readable medium 30. According to the computer program the CPU 41 executes the steps of the computer-implemented method according to the first aspect of example embodiments and schematically depicted in FIG. 1. The execution can be initiated and controlled by a user (e.g. radiologist) via the HID 44. The status and/or result of the executed computer program may be indicated to the user by the MON 45 or output via the I/O 46. The result of the executed computer program may be permanently stored on the non-volatile MEM 43 or another computer-readable medium.

In particular, the CPU 41 and RAM 42 for executing the computer program may comprise several CPUs 41 and several RAMs 42 for example in a computation cluster or a cloud system. The HID 44 and MON 45 for controlling execution of the computer program may be comprised by a different data processing system like a terminal communicatively connected to the data processing system 40 (e.g. cloud system).

In FIG. 5 an example embodiment of the CT system 50 according to the fifth aspect of example embodiments is schematically depicted. The CT system comprises a CT scanner 51, the data processing system 40 of FIG. 4 and an output device, which may be an external device (e.g. monitor, display, printer, etc., not depicted) or the output device MON 45 of the data processing system 40.

The data processing system 40 is communicatively connected to a controller (not depicted) of the CT scanner 51 or integrated in the controller of the CT scanner 51. The data processing system 40 is configured to receive data of projections and additionally or alternatively of volumes of CT scans conducted by the CT scanner 51 via the input module 20, 46 of the data processing system 40 as input for the method according to FIG. 1. Based on the method of FIG. 1 the data processing system 40 provides filtered volumes that may be displayed to a user (e.g. radiologist) via the external display device or the display device MON 45.

Figure 6:
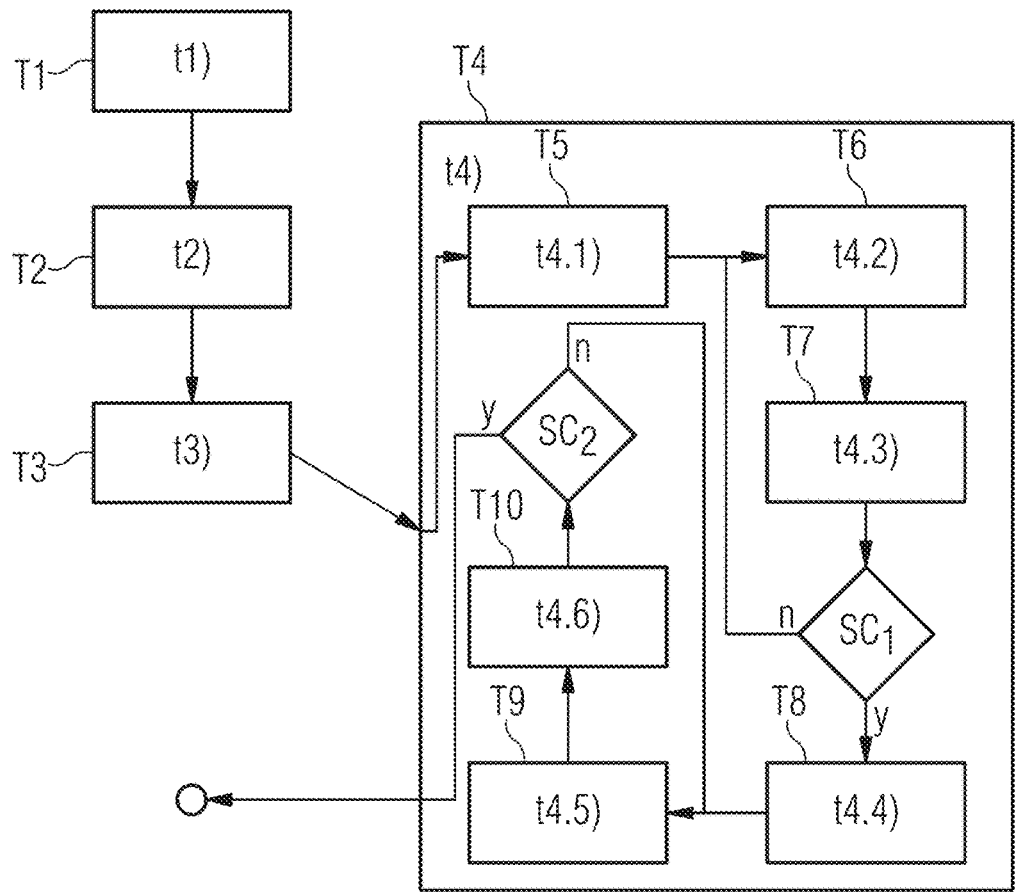
FIG. 6 is a schematic flow chart of the computer-implemented method of training and of the computer program according to the seventh aspect of example embodiments.

In FIG. 6 an example embodiment of the computer-implemented method of training according to the sixth aspect of example embodiments and of the computer program according to the seventh aspect of example embodiments are schematically depicted.

The method of training is used to train the first neural network NNsin (21 in FIG. 7) for automatically tuning one or both of the projection filter parameters σs,sin/σi,sin for the projection (J)BF, F sin (22 in FIG. 7) and the second neural network NNvol (24 in FIG. 7) for automatically tuning one or both of the volume filter parameters σs,vol/σi,vol for the volume (J)BF Fvol (25 in FIG. 7) The method of training comprises the training steps t1) of providing T1 a training set comprising training data of training volumes; t2) of providing T2 a first (untrained) neural network NNsin; t3) of providing T3 a second (untrained) neural network NNvol; and t4) of training 14 the first neural network NNsin and the second neural network NNvol.

In the step t1) the training set for training the two neural networks NNsin, NNvol is provided. The training set comprises the training data that includes data of the training volumes and data of corresponding training projections.

In the step t2) the first (untrained) neural network NNsin is provided. The first neural network NNsin is configured to receive data of projections as input and to provide a spatial projection filter parameter σs,sin and additionally or alternatively an intensity projection filter parameter σi,sin of the projection (J)BF F sin as output.

In the step t3) the second (untrained) neural network NNvol is provided. The second neural network NNvol is configured to receive data of volumes as input and to provide a spatial volume filter parameter σs,vol and additionally or alternatively an intensity volume filter parameter σi,vol of the volume (J)BF Fvol as output.

In the step t4) the first neural network NNsin and the second neural network NNvol are trained based on a respective reward for each of the first and second neural network. In particular, the step t4) comprises the sub-step t4.1) of randomly selecting T5 one or more of the training volumes; and for each selected training volume the sub-steps t4.2) of filtering T6 the current projections; t4.3) of updating T7 weights of the first neural network NNsin; t4.4) of forwarding T8 the volume; t4.5) filtering T9 the current volume; and updating T10 weights of the second neural network NNvol.

In the sub-step t4.1) the one or more of the training volumes to be used for training the first and second neural network are randomly selected from the training volumes comprised in the training set. Either corresponding training projections belonging to the selected training volume comprised in the corresponding training data are selected as the current projections or projections are forward-projected from the selected training volume as the current projections.

For each selected training volume the sub-steps t4.2) to t4.6) executed.

The sub-steps t4.2) and t4.3) are iteratively executed until a first stop criterion SC1 (e.g. a predefined number of iterations) is met.

In the sub-step t4.2) the current projections are filtered with the projection (J)BF F sin which is an analogous or the same (J)BF as described above for the method of FIG. 1. The filtering is based on the projection filter parameters σs,sin, σi,sin tuned by the first neural network NNsin to be trained. Thereby, the first neural network NNsin tunes the projection filter parameters based on current weights of the first neural network NNsin. In the first iteration, the projection filter parameters σs,sin, σi,sin may be set to a predefined value.

In the sub-step t4.3) the weights of the first neural network NNsin are updated based on the reward. The reward is estimated from a volume backward-projected from the filtered projections (in step t4.2)) and a volume backward-projected based on the current projections. In case the predefined first stop criterion SC1 is not met, the filtered projections are forwarded as the current projections and a next iteration is started at sub-step t4.2).

In the sub-step t4.4), in case the first stop criterion SC1 was met, the volume backward-projected from the filtered projections (in step t4.2)) is forwarded as the current volume.

The sub-steps t4.5) and t4.6) are iteratively executed until a second stop criterion SC2 (e.g. a predefined number of iterations) is met.

In the sub-step t4.5) the current volume is filtered with the volume (J)BF Fvol which is an analogous or the same (J)BF as described above for the method of FIG. 1. The filtering is based on the volume filter parameters σs,vol, σi,vol tuned by the second neural network NNvol to be trained. Thereby, the second neural network NNvol tunes the volume filter parameters based on current weights of the second neural network NNvol. In the first iteration, the volume filter parameters σs,vol, σi,vol may be set to a predefined value.

In the sub-step t4.6) weights of the second neural network NNvole are updated based on the reward. The reward is estimated from the filtered volume (in step t4.5)) and the current volume. In case the predefined second stop criterion SC2 is not met, the filtered volume is forwarded as the current volume and a next iteration is started at sub-step t4.5).

Preferably, the first neural network NNsin and additionally or alternatively the second neural network NNvol is trained by a Q-learning approach based on the reward estimated using a reward network Nrew (27). The weights of the first neural network NNsin are updated based on the reward estimated from the backward-projected filtered projections and backward-projected current projections using the reward network Nrew. The weights of the second neural network NNvol are updated based on the reward estimated from the filtered volume and current volume using the reward network Nrew.

In particular, the reward network Nrew may be a neural network trained to predict a quality score IRQM for estimating the reward.

Figure 7:
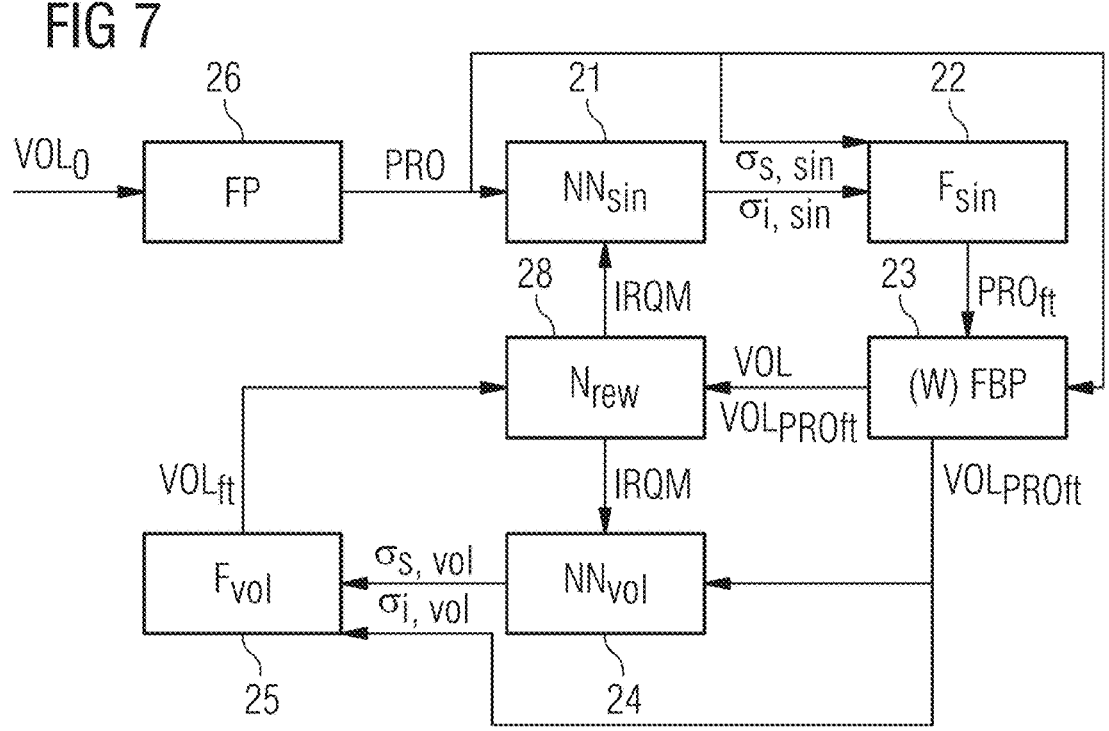
FIG. 7 is a schematic view of the first and second neural network NNsin, NNvol to be trained; the reward network Nrew; the projection and volume (J)BF F sin, Fvol; the backward-projector; and the forward-projector.

In FIG. 7 an example embodiment of the first and second neural network NNsin, NNvol to be trained; the reward network Nrew; the projection and volume (J)BF F sin, Fvol; the backward-projector; and the forward-projector is schematically depicted. The elements and entities labelled with the same reference sign as in FIG. 2 are the same or corresponding entities as those of FIG. 2 described above. Consequently, only differences to the example embodiment of FIG. 2 are described.

There is no explicit input and output module present. The reward network Nrew may be implemented on a reward module 28, which may be a software module (e.g. a class) or a hardware module (e.g. a processing unit). The reward module 28 is communicatively connected to the first filter module 23 for receiving backward-projected volume VOL, which is backward-projected from the current projections, and the backward-projected volume VOLPROft, which is backward-projected from the filtered projections. The reward module 28 is further communicatively connected to the second filter module 25 for receiving the filtered volume VOLft. Moreover, the reward module 28 is communicatively connected to the first machine learning module 21 and to the second machine learning module 24 for forwarding the respective reward.

For each of the one or more selected training volumes the training data of the training volume VOL0 is provided to the forward-projector module 26. Based on the training volume VOL0 projections PRO are forward-projected using the forward-projection FP and provided to the first machine learning module 21 as the current projections. In case data of training projections is comprised in the training data of the randomly selected volume(s), said training projections are directly provided to the first machine learning module 21 as the current projections.

The current projections PRO are used to automatically tune the projection filter parameter(s) based on the current weights of the first neural network NNsin. The automatically tuned projection filter parameters are forwarded to the first filter module 22 and used in filtering the current projections with the projection (J)BF. In particular, for each of the current projections a respective pair of projection filter parameters may be automatically tuned and used in filtering.

The resulting filtered projections PROft are used in forward-projecting the volume VOLPROft by the (W)FBP. The (unfiltered) current sinograms PRO are used in forward-projecting the volume VOL by the (W)FBP. Both volumes are forwarded to the reward module 28.

Based on the two volumes VOLPROft, VOL the reward network Nrew estimates a reward IRQM, that is forwarded to the first machine learning module 21 and used for adjusting the weights of the first neural network NNsin.

After the first stop criterion SC1 is met, the forward-projected the volume VOLPROft is forwarded to the second machine learning module 24 as the current volume.

The current volume VOLPROft is used to automatically tune the volume filter parameter(s) based on the current weights of the second neural network NNvol. The automatically tuned volume filter parameters are forwarded to the second filter module 24 and used in filtering the current volume with the volume (J)BF. In particular, for each of the voxels of the current volume a respective pair of volume filter parameters may be automatically tuned and used in filtering.

The resulting filtered volume VOLft and the current volume VOLPROft are forwarded to the reward module 28.

Based on the two volumes VOLft, VOLPROft the reward network Nrew estimates a reward IRQM, that is forwarded to the second machine learning module 24 and used for adjusting the weights of the second neural network NNvol.

After the second stop criterion SC2 is met, the training is either continued with the next randomly selected training volume or ended.

Figure 8:
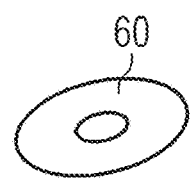
FIG. 8 is a schematic view of the computer-readable medium having stored thereon the computer program according to the seventh aspect of example embodiments.

In FIG. 8 an example embodiment of the computer-readable medium 60 according to the eighth aspect of example embodiments is schematically depicted.

Here, exemplarily a computer-readable storage disc 60 like a Compact Disc (CD), Digital Video Disc (DVD), High Definition DVD (HD DVD) or Blu-ray Disc (BD) has stored thereon the computer program according to the seventh aspect of example embodiments and as schematically depicted in FIG. 6. However, the computer-readable medium may also be a data storage like a magnetic storage/memory (e.g. magnetic-core memory, magnetic tape, magnetic card, magnet strip, magnet bubble storage, drum storage, hard disc drive, floppy disc or removable storage), an optical storage/memory (e.g. holographic memory, optical tape, Tesa tape, Laserdisc, Phasewriter (Phasewriter Dual, PD) or Ultra Density Optical (UDO)), a magneto-optical storage/memory (e.g. MiniDisc or Magneto-Optical Disk (MO-Disk)), a volatile semiconductor/solid state memory (e.g. Random Access Memory (RAM), Dynamic RAM (DRAM) or Static RAM (SRAM)) or a non-volatile semiconductor/solid state memory (e.g. Read Only Memory (ROM), Programmable ROM (PROM), Erasable PROM (EPROM), Electrically EPROM (EEPROM), Flash-EEPROM (e.g. USB-Stick), Ferroelectric RAM (FRAM), Magnetoresistive RAM (MRAM) or Phase-change RAM).

Figure 9:
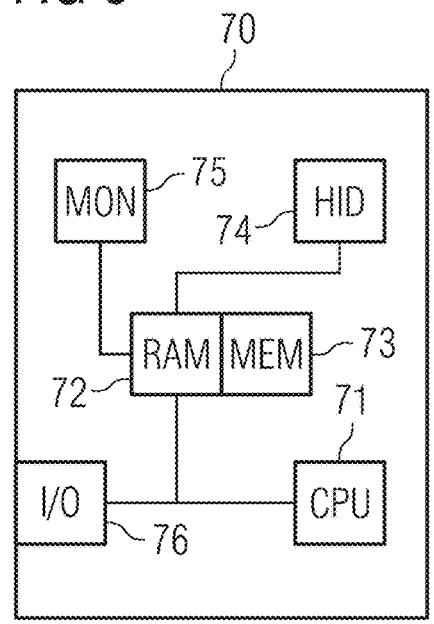
FIG. 9 is a schematic view of the data processing system according to the ninth aspect of example embodiments.

In FIG. 9 an example embodiment of the data processing system 70 according to the ninth aspect of example embodiments is schematically depicted. The data processing system 70 may be a personal computer (PC), a laptop, a tablet, a server, a distributed system (e.g. cloud system) and the like. The data processing system 70 comprises a central processing unit (CPU) 71, a memory having a random-access memory (RAM) 72 and a non-volatile memory (MEM, e.g. hard disk) 73, a human interface device (HID, e.g. keyboard, mouse, touchscreen etc.) 74, an output device (MON, e.g. monitor, printer, speaker, etc.) 75 and an interface (I/O) 76 for receiving and sending data. The CPU 71, RAM 72, HID 74, MON 75 and I/O 46 are communicatively connected via a data bus. The RAM 72 and MEM 73 are communicatively connected via another data bus.

The computer program according to the seventh aspect of example embodiments and schematically depicted in FIG. 6 can be loaded into the RAM 72 from the MEM 73 or another computer-readable medium 60. According to the computer program the CPU 71 executes the steps of the computer-implemented method of training according to the sixth aspect of example embodiments and schematically depicted in FIG. 6. The execution can be initiated and controlled by a user via the HID 74. The status and/or result of the executed computer program may be indicated to the user by the MON 75 or output via the I/O 76. The result of the executed computer program may be permanently stored on the non-volatile MEM 73 or another computer-readable medium.

In particular, the CPU 71 and RAM 72 for executing the computer program may comprise several CPUs 71 and several RAMs 72 for example in a computation cluster or a cloud system. The HID 74 and MON 75 for controlling execution of the computer program may be comprised by a different data processing system like a terminal communicatively connected to the data processing system 70 (e.g. cloud system).

Figure 10:
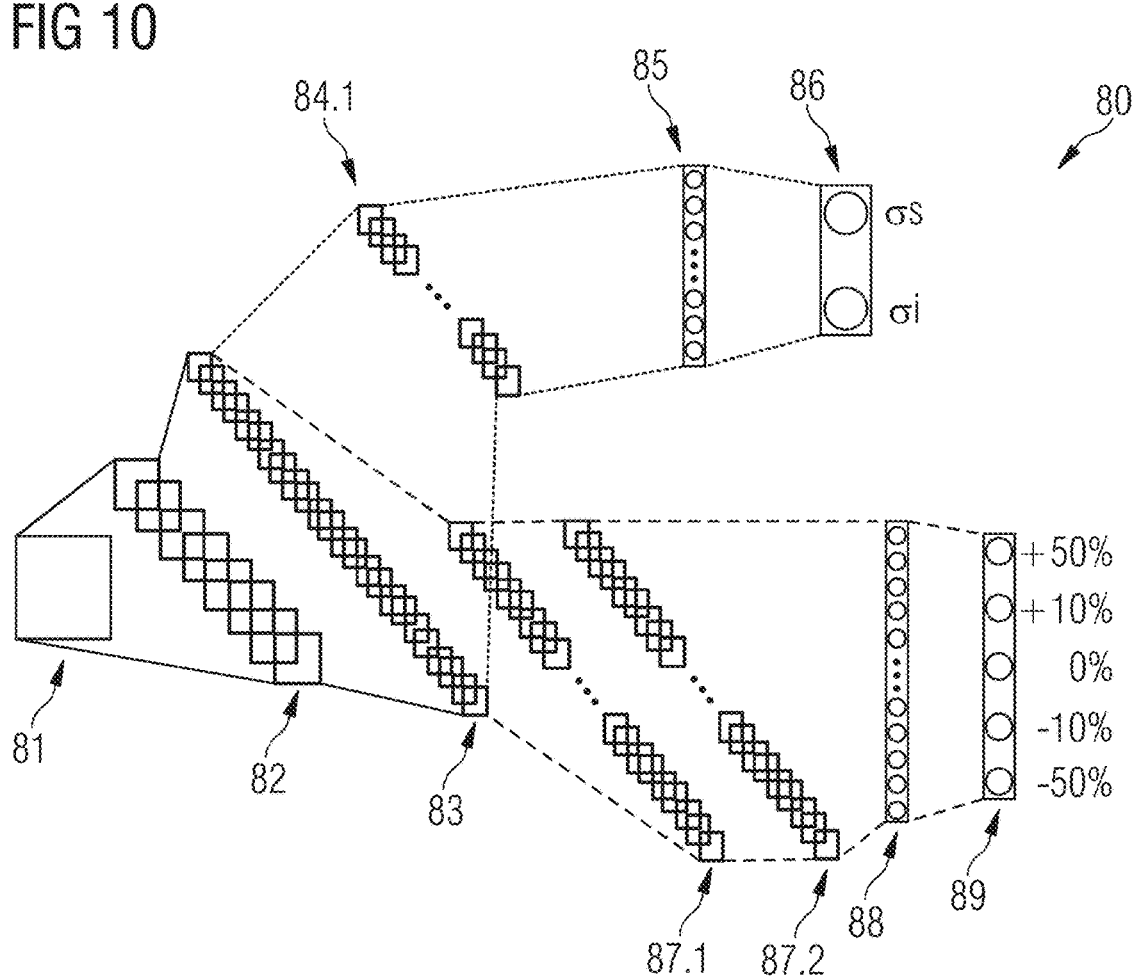
FIG. 10 is a schematic view of the architecture of the first or second neural network NNsin, NNvol.

In FIG. 10 an example embodiment of the architecture of the first or second neural network NNsin, NNvol is schematically depicted. In particular, the first neural network NNsin may be a 2D convolutional neural network (CNN) and the NNvol may be a 3D CNN. In the following, the NNvol having a 3D CNN architecture is exemplarily described. For the NNsin an analogous architecture with filters having 2D kernels (L×W) instead of 3D kernels (L×W×D) can be utilized.

The CNN 80 comprises an input layer 81; a first layer 82; a second layer 83; and a parameter branch as well as an action branch. The parameter branch comprises a first parameter layer 84.1; a parameter condensation layer 85; and a parameter output layer 86. The action branch comprises a first action layer 87.1; a second action layer 87.2, an action condensation layer 88; and an action output layer 89.

The input layer 81 is configured to receive a 3D tensor (i.e. volume) of a predefined size (e.g. 9×9×5) as input. In particular, a patch of the respective volume, for which the CNN 80, here the second neural network NNvol, is to automatically tune the volume filter parameters, is received as input.

The first layer 82 comprises 32 filters subsequent to the input layer 81, wherein each filter reduces the size of the input and may have a 3D kernel of 5×5×3.

The second layer 83 comprises 64 filters subsequent to the first layer 82, wherein each filter reduces the size of the input and may have a 3D kernel of 3×3×1.

In the parameter branch (upper branch in FIG. 10) subsequent to the second layer 83, the first parameter layer 84.1 comprises 64 filters, wherein each filter reduces the size of the input and may have a 2D kernel of 3×3.

The parameter condensation layer 85 comprises 128 (1D) nodes subsequent to the first parameter layer 84.1.

The parameter output layer 86 comprises two nodes, one node for each of the two filter parameters. Thus, the parameter branch is configured and trained to select one of the two filter parameters to be tuned.

In the action branch (lower branch in FIG. 10) subsequent to the second layer 83, the first action layer 87.1 comprises 128 filters, wherein each filter reduces the size of the input and may have a 2D kernel of 3×3.

The second action layer 87.2 comprises 128 filters subsequent to the first action layer 87.1, wherein each filter may have a 2D kernel of 3×3.

The action condensation layer 88 comprises 256 (1D) nodes subsequent to the second action layer 87.2.

The action output layer 89 comprises five nodes, one node for each possible action to change the filter parameter. Thus, the action branch is configured and trained to select one of the five actions to change the value of the selected filter parameter to be tuned.

Figure 11:
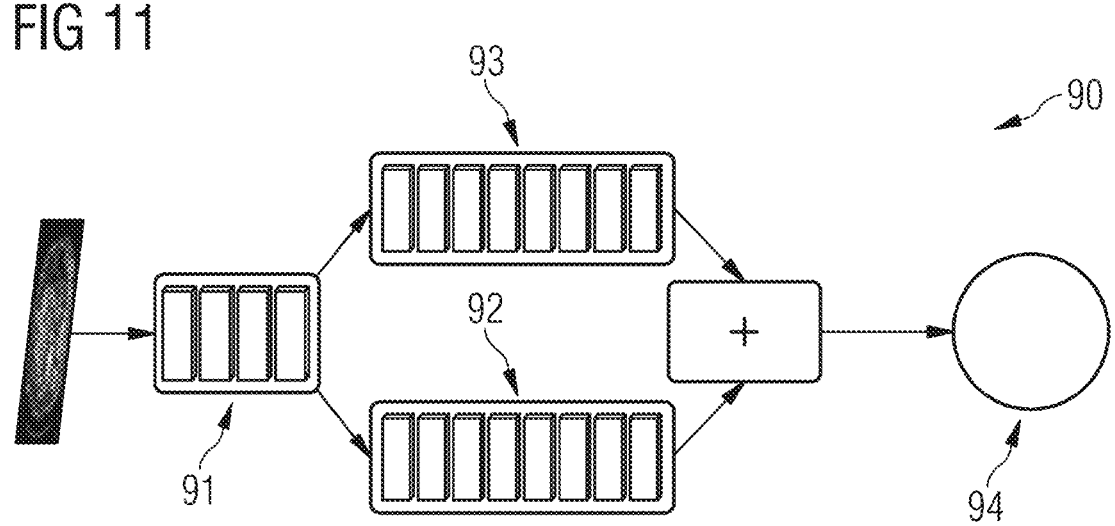
FIG. 11 is a schematic view of a possible architecture of the reward network Nrew.

In FIG. 11 an example embodiment of a possible architecture 90 of the reward network Nrew is schematically depicted. The architecture 90 used for the reward network Nrew comprises a feature extracting module 91; an observer module 92; estimation module 93; and an output module 94.

The feature extracting module 91 is configured to extract (hidden) features from an input volume (e.g. a forward-projected volume from filtered projections or a filtered volume) which are forwarded to the observer module 92 and to the estimation module 93.

The observer module 92 is configured to calculate model observer scores from the received features.

The estimation module 93 is configured to estimate a noise and/or quality based on the received features.

Based on the calculated model observer scores and estimated noise/quality the (optimizable) reward is output at the output module 94.

In FIG. 12 an example embodiment of the architecture of the CNN 100 used as reward network Nrew is schematically depicted. The CNN 100 comprises a first (input) layer 101 having 16 filters; a subsequent second layer 102 having 16 filters; a subsequent third layer 103 having 32 filters; a subsequent fourth layer 104 having 32 filters; a subsequent fifth layer 105 having 64 filters; a subsequent sixth layer 106 having 128 filters; a subsequent seventh layer 107 having 256 filters; a subsequent eighth layer 108 having 512 filters; a GAP layer 109; a final layer 110 having 512 nodes; and an output layer 111.

The CNN 100 is configured and trained to estimate a quality measure, in particular the IRQM for input volumes, without any reference (e.g. noise-free reference volume) and output the latter via the output layer 111.

Although specific embodiments have been illustrated and described herein, it will be appreciated by those of ordinary skill in the art that a variety of alternate and/or equivalent implementations exist. It should be appreciated that the example embodiment or example embodiments are only examples, and are not intended to limit the scope, applicability, or configuration in any way. Rather, the foregoing summary and detailed description will provide those skilled in the art with a convenient road map for implementing at least one example embodiment, it being understood that various changes may be made in the function and arrangement of elements described in an example embodiment without departing from the scope as set forth in the appended claims and their legal equivalents. Generally, this application is intended to cover any adaptations or variations of the specific embodiments discussed herein.

In the foregoing detailed description, various features are grouped together in one or more examples for the purpose of streamlining the disclosure. It is understood that the above description is intended to be illustrative, and not restrictive. It is intended to cover all alternatives, modifications and equivalents as may be included within the scope of this disclosure. Many other examples will be apparent to one skilled in the art upon reviewing the above specification.

Specific nomenclature used in the foregoing specification is used to provide a thorough understanding of the example embodiments. However, it will be apparent to one skilled in the art in light of the specification provided herein that the specific details are not required in order to practice embodiments of the present invention. Thus, the foregoing descriptions of specific example embodiments are presented for purposes of illustration and description. They are not intended to be exhaustive or to limit the disclosure or claims to the precise forms disclosed; obviously many modifications and variations are possible in view of the above teachings. The embodiments were chosen and described in order to best explain the principles of embodiments of the present invention and its practical applications, to thereby enable others skilled in the art to best utilize embodiments of the present invention and various example embodiments with various modifications as are suited to the particular use contemplated. Throughout the specification, the terms "including" and "in which" are used as the plain-English equivalents of the respective terms "comprising" and "wherein," respectively. Moreover, the terms "first," "second," and "third," etc., are used merely as labels, and are not intended to impose numerical requirements on or to establish a certain ranking of importance of their objects. In the context of the present description and claims the conjunction "or" is to be understood as including ("and/or") and not exclusive ("either . . . or").

What is claimed is:

1. A computer-implemented method of iteratively reconstructing images or a volume using deep learning, the computer-implemented method comprising:
    first automatically tuning at least one of a spatial projection filter parameter or an intensity projection filter parameter of a projection bilateral filter by a first trained neural network based on (i) data of projections of an imaging procedure in case a first iteration starts at the first automatically tuning or (ii) data of forward projected projections, otherwise;
    filtering the projections with the projection bilateral filter using at least one automatically tuned projection filter parameter;
    backward-projecting a volume from (i) the projections of the imaging procedure, in case the first iteration starts at the backward projecting, or (ii) the filtered projections, otherwise, using a filtered back-projection;
    second automatically tuning at least one of a spatial volume filter parameter or an intensity volume filter parameter of a volume filter by a second trained neural network based on (i) data of a volume of the imaging procedure, in case the first iteration starts at the second automatically tuning, or (ii) the backward-projected volume, otherwise;
    filtering the volume with the volume filter using at least one automatically tuned volume filter parameter;
    forward-projecting projections from (i) the volume of the imaging procedure, in case the first iteration starts at the forward-projecting, or (ii) the filtered volume and returning to the first automatically tuning, in case the filtered volume does not meet a threshold quality criterion, otherwise, or outputting the filtered volume as the reconstructed images or volume, in case the filtered volume meets the threshold quality criterion; and
    wherein the first iteration starts at one of the first automatically tuning, the backward-projecting, the second automatically tuning or the forward-projecting.

2. The method according to claim 1, wherein at least one of the spatial projection filter parameter or the intensity projection filter parameter is tuned for each of the projections.

3. The method according to claim 1, wherein at least one of the spatial volume filter parameter or the intensity volume filter parameter is tuned for each voxel of the volume.

4. The method according to claim 1, wherein at least one of the first trained neural network or the second trained neural network is configured to automatically select one of the at least one of the spatial projection filter parameter or the intensity projection filter parameter, to be tuned.

5. The method according to claim 1, wherein at least one of the first trained neural network or the second trained neural network is configured to output one of a number of actions to tune at least one respective filter parameter.

6. The method according to claim 5, wherein the number of actions to tune the at least one respective filter parameter comprises:
    increasing a parameter value by 50%;
    increasing the parameter value by 10%;
    not changing the parameter value;
    decreasing the parameter value by 10%; or
    decreasing the parameter value by 50%.

7. A non-transitory computer-readable storage medium storing computer-executable instructions that, when executed on a data processing system, cause the data processing system to execute the method according to claim 1.

8. A data processing system comprising:
    an input module configured to receive at least one of projections or volumes of an imaging procedure;
    an output module configured to be communicatively connected with, and to provide, volumes to external modules;
    a projection bilateral filter configured to filter the projections;
    a volume filter configured to filter the volumes;
    a backward-projector communicatively connected to the volume filter, and configured to backward-project volumes from the projections;
    a forward-projector communicatively connected to the volume filter, and configured to forward-project projections from the volumes;
    a first trained neural network communicatively connected to the forward-projector, and configured to receive data of projections as input, and to provide at least one of a spatial projection filter parameter or an intensity projection filter parameter of the projection bilateral filter as output;
    a second trained neural network communicatively connected to the backward-projector, and configured to receive data of a volume as input, and to provide at least one of a spatial volume filter parameter or an intensity volume filter parameter of the volume filter as output;
    wherein the input module is communicatively connected to at least one of the first trained neural network, the second trained neural network, the backward-projector, or the forward-projector;
    wherein the first trained neural network is configured to automatically tune at least one of the spatial projection filter parameter or the intensity projection filter parameter based on the data of the projections or on data of the forward-projected projections;

wherein the projection bilateral filter is configured to filter the projections using at least one projection filter parameter;

wherein the backward-projector is configured to backward-project a volume from the projections or from the filtered projections, using a filtered back-projection;

wherein the second trained neural network is configured to automatically tune at least one of the spatial volume filter parameter or the intensity volume filter parameter of the volume filter based on the data of the volume or on the backward-projected volume;

wherein the volume filter is configured to filter the volume using at least one volume filter parameter;

wherein the forward-projector is configured to forward-project projections from the volume or from the filtered volume; and wherein the output module is communicatively connected to the volume filter, and configured to provide the filtered volume to the external modules, in case the filtered volume meets a quality criterion.

9. A CT system, comprising:
a CT scanner;
the data processing system according to claim 8 communicatively connected to a controller of the CT scanner or integrated in the controller of the CT scanner; and
an output device communicatively connected to the data processing system;
wherein the data processing system is configured to receive data of at least one of projections or of volumes of CT scans conducted by the CT scanner via the input module of the data processing system as input; and
wherein the data processing system is configured to provide filtered volumes to the output device via the output module of the data processing system.

10. A computer-implemented method of training a first neural network for automatically tuning a projection filter parameter for a projection bilateral filter, and a second neural network for automatically tuning a volume filter parameter for a volume filter, the computer-implemented method comprising:
providing a training set including training data of training volumes;
providing the first neural network configured to receive data of projections as input, and to provide at least one of a spatial projection filter parameter or an intensity projection filter parameter of the projection bilateral filter as output;
providing a second neural network configured to receive data of a volume as input, and to provide at least one of a spatial volume filter parameter or an intensity volume filter parameter of the volume filter as output; and
training the first neural network and the second neural network based on a respective reward for the first neural network and the second neural network.

11. The method according to claim 10, wherein the training the first neural network and the second neural network comprises:
randomly selecting one or more of the training volumes and selecting, as current projections, either training projections included in the a corresponding training data or forward-projecting projections from the selected one or more of the training volumes; and
for each selected training volume
first filtering the current projections with the projection bilateral filter based on at least one projection filter parameter tuned by the first neural network based on current weights of the first neural network, updating weights of the first neural network based on a reward estimated from a volume backward-projected from the first filtered current projections and a volume backward-projected based on the current projections and, in case a first stop criterion is not met, forwarding the filtered projections as the current projections and returning to the first filtering, forwarding the volume backward-projected from the first filtered current projections as a current volume, second filtering the selected training volume with the volume filter based on at least one volume filter parameter tuned by the second neural network based on current weights of the second neural network, and updating weights of the second neural network based on a reward estimated from the filtered training volume and the selected training volume and, in case a second stop criterion is not met, forwarding the filtered training volume as the selected training volume and returning to the second filtering.

12. The method according to claim 10, wherein at least one of
the first neural network is trained by a Q-learning approach based on a reward estimated using a reward network, wherein weights of the first neural network are updated based on the reward estimated from backward-projected filtered projections and backward-projected current projections using the reward network, or
the second neural network is trained by a Q-learning approach based on the reward estimated using the reward network, wherein weights of the second neural network are updated based on the reward estimated from a filtered volume and a selected training volume using the reward network.

13. The method according to claim 12, wherein the reward network is a neural network trained to predict a quality score for estimating the reward.

14. A non-transitory computer-readable storage medium storing computer-executable instructions that, when executed on a data processing system, cause the data processing system to execute the method according to claim 10.

15. A data processing system, comprising:
a memory storing computer-executable instructions; and
one or more processors configured to execute the computer-executable instructions to cause the data processing system to perform the method according to claim 10.

16. The method according to claim 2, wherein at least one of the first trained neural network or the second trained neural network is configured to automatically select one of the at least one of the spatial projection filter parameter or intensity projection filter parameter, to be tuned.

17. The method according to claim 3, wherein at least one of the first trained neural network or the second trained neural network is configured to automatically select one of the at least one of the spatial projection filter parameter or intensity projection filter parameter, to be tuned.

18. The method according to claim 2, wherein at least one of the spatial volume filter parameter or the intensity volume filter parameter are tuned for each voxel of the volume.

19. The method according to claim 2, wherein at least one of
the first trained neural network is configured to output one of a number of actions to tune the at least one of the spatial projection filter parameter or the intensity projection filter parameter, or the second trained neural network is configured to output one of a number of actions to tune the at least one of the spatial volume filter parameter or the intensity volume filter parameter.

20. The method according to claim 3, wherein at least one of
the first trained neural network is configured to output one of a number of actions to tune the at least one of the spatial projection filter parameter or the intensity projection filter parameter, or
the second trained neural network is configured to output one of a number of actions to tune the at least one of the spatial volume filter parameter or the intensity volume filter parameter.

21. The method according to claim 4, wherein at least one of the first trained neural network or the second trained neural network is configured to output one of a number of actions to tune the respective filter parameter(s).

22. The method according to claim 11, wherein at least one of
the first neural network is trained by a Q-learning approach based on a reward estimated using a reward network, wherein weights of the first neural network are updated based on the reward estimated from backward-projected filtered projections and backward-projected current projections using the reward network, or
the second neural network is trained by a Q-learning approach based on the reward estimated using the reward network, wherein weights of the second neural network are updated based on the reward estimated from a filtered volume and a selected training volume using the reward network.

* * * * *